(12) United States Patent
Kai et al.

(10) Patent No.: US 8,722,208 B2
(45) Date of Patent: May 13, 2014

(54) ORGANIC ELECTROLUMINESCENT DEVICE

(75) Inventors: Takahiro Kai, Kitakyushu (JP); Hideki Tanaka, Kitakyushu (JP); Mitsuru Suda, Kitakyushu (JP); Toshihiro Yamamoto, Kitakyushu (JP); Megumi Matsumoto, Kitakyushu (JP)

(73) Assignee: Nippon Steel & Sumikin Chemical Co., Ltd., Tokyo (JP)

( * ) Notice: Subject to any disclaimer, the term of this patent is extended or adjusted under 35 U.S.C. 154(b) by 192 days.

(21) Appl. No.: 13/146,238

(22) PCT Filed: Feb. 25, 2010

(86) PCT No.: PCT/JP2010/052966
§ 371 (c)(1),
(2), (4) Date: Jul. 26, 2010

(87) PCT Pub. No.: WO2010/098386
PCT Pub. Date: Sep. 2, 2010

(65) Prior Publication Data
US 2011/0284828 A1    Nov. 24, 2011

(30) Foreign Application Priority Data

Feb. 27, 2009 (JP) ................................. 2009-046472

(51) Int. Cl.
*H01L 51/54* (2006.01)
(52) U.S. Cl.
USPC ........... 428/690; 428/917; 313/504; 313/505; 313/506; 546/21; 546/255; 546/256; 546/257; 546/264; 546/268.1; 546/276.1
(58) Field of Classification Search
USPC .................. 428/690, 917; 313/504, 505, 506; 546/21, 255, 256, 257, 264, 268.1, 546/276.7; 544/180, 194, 212, 214
See application file for complete search history.

(56) References Cited

U.S. PATENT DOCUMENTS

| 2009/0167166 A1* | 7/2009 | Bach et al. ..................... 313/504 |
| 2011/0012100 A1 | 1/2011 | Stoessel |
| 2011/0057184 A1 | 3/2011 | Kai et al. |

FOREIGN PATENT DOCUMENTS

| JP | 2006-073581 A | 3/2006 |
| JP | 2008-244013 A | 10/2008 |
| WO | WO 2009/118087 A1 | 10/2009 |
| WO | WO 2009/136586 A1 | 11/2009 |

OTHER PUBLICATIONS

English translation of International Preliminary Report on Patentability issued Sep. 9, 2011, in PCT International Application No. PCT/JP2010/052966.
Polikarpov et al., "Emission zone control in blue organic electrophosphorescent devices through chemical modification of host materials," Applied Physics Letters (2010) vol. 96, pp. 053306-1-053306-3.

\* cited by examiner

*Primary Examiner* — Gregory Clark
(74) *Attorney, Agent, or Firm* — Birch, Stewart, Kolasch & Birch, LLP

(57) ABSTRACT

Disclosed is an organic electroluminescent device (organic EL device) which is improved in luminous efficiency, fully secured of high driving stability, and of a simple structure. The organic EL device is constituted of an anode, organic layers containing a phosphorescent light-emitting layer, and a cathode piled one upon another on a substrate and a phosphine oxide derivative represented by general formula (1) is contained in a phosphorescent light-emitting layer, an electron-transporting layer, a hole-blocking layer, or an exciton-blocking layer. In general formula (1), $L_1$ is a direct bond or an aromatic group with a valence of 1-3 and $Ar_1$ is an aromatic group. The two $Ar_1$ groups linked to the same nitrogen atom may form a nitrogen heterocycle and may further form a fused ring together with the said nitrogen heterocycle.
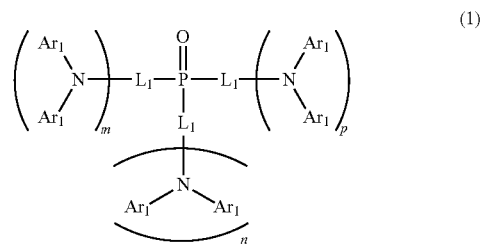
(1)
4 Claims, 1 Drawing Sheet

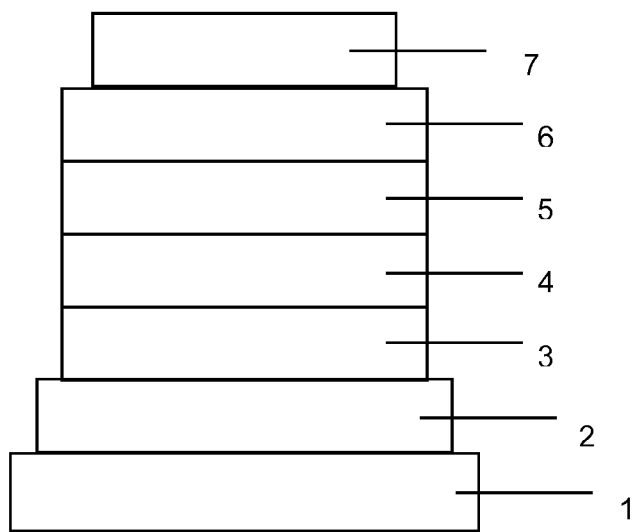

ORGANIC ELECTROLUMINESCENT DEVICE

TECHNICAL FIELD

This invention relates to an organic electroluminescent device comprising a phosphine oxide derivative and, more particularly, to a thin film device that emits light upon application of an electrical field to a light-emitting layer composed of an organic compound.

An organic electroluminescent device (hereinafter referred to as organic EL device) in the simplest structure is generally constituted of a light-emitting layer and a pair of counter electrodes sandwiching the said light-emitting layer. The device functions by utilizing the following phenomenon; upon application of an electrical field between the electrodes, electrons are injected from the cathode and holes are injected from the anode and they recombine in the light-emitting layer with emission of light.

In recent years, organic thin films have been used in the development of organic EL devices. In particular, in order to enhance the luminous efficiency, the kind of electrodes has been optimized for the purpose of improving the efficiency of injecting carriers from the electrodes and a device has been developed in which a hole-transporting layer composed of an aromatic diamine and a light-emitting layer composed of 8-hydroxyquinoline aluminum complex (hereinafter referred to as Alq3) are disposed in thin film between the electrode. This device has brought about a marked improvement in the luminous efficiency over the conventional devices utilizing single crystals of anthracene and the like and thereafter the developmental works of organic EL devices have been directed toward commercial applications to high-performance flat panels featuring self-luminescence and high-speed response.

In another effort to enhance the luminous efficiency of the device, the use of phosphorescence in place of fluorescence is investigated. The aforementioned device comprising a hole-transporting layer composed of an aromatic diamine and a light-emitting layer composed of Alq3 and many others utilize fluorescence. The use of phosphorescence, that is, emission of light from the excited triplet state, is expected to enhance the luminous efficiency three to four times that of the conventional devices utilizing fluorescence (emission of light from the excited singlet state). To achieve this objective, the use of coumarin derivatives and benzophenone derivatives in the light-emitting layer was investigated, but these derivatives merely produced luminance at an extremely low level. Europium complexes were also investigated in trials to utilize the excited triplet state, but they failed to emit light at high efficiency. In recent years, as stated in patent document 1, a large number of researches are conducted with the objective of enhancing the luminous efficiency and extending the lifetime while giving priority to utilization of organic metal complexes such as iridium complexes.

Patent document 1: JP2003-515897 A
Patent document 2: JP2001-313178 A
Patent document 3: JP2003-317965 A
Patent document 4: JP2007-129206 A
Patent document 5: JP2002-063989 A
Patent document 6: JP2004-095221 A
Patent document 7: JP2004-204140 A
Patent document 8: WO2007137725
Patent document 9: JP2008-244012 A
Non-patent document 1: Applied Physics Letters, 2003, 83, 569-571
Non-patent document 2: Applied Physics Letters, 2003, 82, 2422-2424

In order to enhance the luminous efficiency, a host material to be used together with the aforementioned dopant material becomes important. Of the host materials proposed thus far, a typical example is 4,4'-bis(9-carbazolyl)biphenyl (hereinafter referred to as CBP), a carbazole compound cited in patent document 2. When used as a host material for tris(2-phenylpyridine)iridium complex (hereinafter referred to as Ir(ppy)3), a typical phosphorescent green light-emitting material, CBP displays relatively good luminous characteristics. On the other hand, when used as a host material for phosphorescent blue light-emitting materials, CBP fails to perform at sufficiently high luminous efficiency. This occurs for the following reason; the energy level of the lowest triplet excited state of CBP is lower than that of ordinary phosphorescent blue light-emitting materials and the triplet excitation energy of a phosphorescent blue light-emitting material is transferred to CBP. That is to say, if a phosphorescent host material were designed to have triplet excitation energy higher than that of a phosphorescent light-emitting material, the triplet excitation energy of the phosphorescent light-emitting material would be confined effectively and, as a result, the luminous efficiency would be enhanced. As described in non-patent document 1, the structure of CBP is modified to increase the triplet excitation energy for the purpose of improving this energy-confining effect and the host material thus modified enhances the luminous efficiency of bis[2-(4,6-difluorophenyl)pyridinato-N,C2']iridium picolinate (hereinafter referred to as Flrpic). Further, as described in non-patent document 2, the luminous efficiency is enhanced similarly by using 1,3-dicarbazolylbenzene (hereinafter referred to as mCP) as a host material. However, these materials were not satisfactory for practical use, particularly from the viewpoint of durability.

Moreover, a host material needs to have a good balance of injection/transport properties of electrical charges (holes and electrons) in order to enhance the luminous efficiency. The electron transport ability is inferior to the hole transport ability in the case of CBP and this destroys the balance of electrical charges in the light-emitting layer and causes excess holes to flow out to the side of the cathode thereby reducing the probability of recombination of holes and electrons in the light-emitting layer and eventually lowering the luminous efficiency. Furthermore, in this case, the recombination zone in the light-emitting layer is limited to a narrow region in the vicinity of the interface on the cathode side; consequently, when an electron-transporting material like Alq3 whose energy level of the lowest triplet excited state is lower than that of Ir(ppy)3 is used, there may arise the possibility that the luminous efficiency becomes lower due to transfer of the triplet excitation energy from the dopant to the electron-transporting material.

As described in the aforementioned examples, it is understandable that a host material that has high triplet excitation energy and is balanced well in the injection/transport properties of electrical charges (holes and electrons) is needed in order for an organic EL device to perform at high luminous efficiency. Furthermore, it is desirable that such a host material shows electrochemical stability, high heat resistance, and excellent stability in the amorphous form. However, none of the known host materials satisfies these properties on a practical level at the present.

In patent documents 3-9, some compounds having a specified phosphine oxide skeleton are disclosed for use in organic EL devices.

In patent document 3, examples of the use of a phosphine oxide compound illustrated below (Compound 3) as a phosphorescent host material are disclosed.

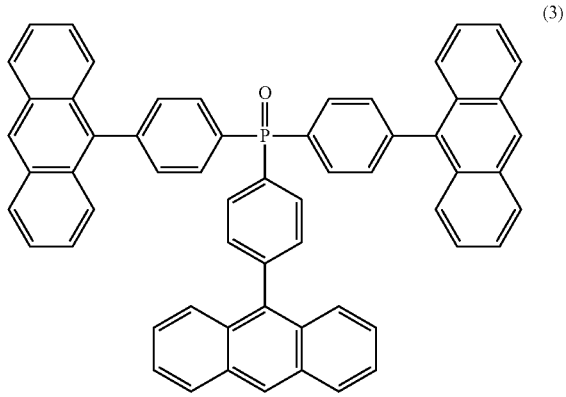 [SMILES: O=P(c1ccc(-c2c3ccccc3cc3ccccc23)cc1)(c1ccc(-c2c3ccccc3cc3ccccc23)cc1)c1ccc(-c2c3ccccc3cc3ccccc23)cc1]

(3)

In the case where a compound has a structure of widely extended conjugation like Compound 3, the triplet excitation energy of the compound becomes too low to effectively confine the triplet excitation energy of a phosphorescent light-emitting material. Moreover, the compound in question lacks sufficient hole transport ability as it is free of substituents having a hole transport property and the balance of electrical charges in the light-emitting layer is destroyed to reduce the probability of recombination of electrons and holes. For this reason, the use of a compound of this kind as a phosphorescent host material cannot enhance the luminous efficiency.

In patent document 4, a phosphine oxide compound (Compound 4) that contains carbazolyl groups as substituents having a hole transport property is disclosed as a material for organic EL devices.

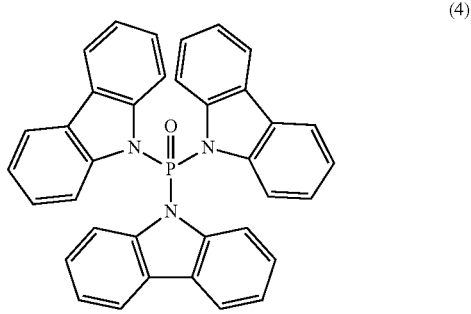 [SMILES: O=P(n1c2ccccc2c2ccccc21)(n1c2ccccc2c2ccccc21)n1c2ccccc2c2ccccc21]

(4)

However, the said compound cannot fully display its electron transport ability as the phosphine oxide group having an electron transport ability is surrounded by three bulky carbazolyl groups. For this reason, the balance of electrical charges in the light-emitting layer is destroyed to reduce the probability of recombination of electrons and holes.

In patent documents 5-8, phosphine oxide compounds in which a diarylamino group or a carbazolyl group is linked through an aromatic linking group as a substituent having a hole transport property are disclosed as fluorescent host materials, materials for use in organic thin films adjacent to the light-emitting layer, and electron-transporting materials. The aforementioned phosphine oxide compounds are Compounds 5-8, respectively illustrated by formulas (5)-(8).

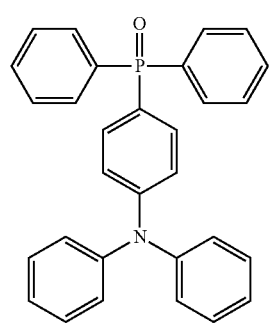

(5)

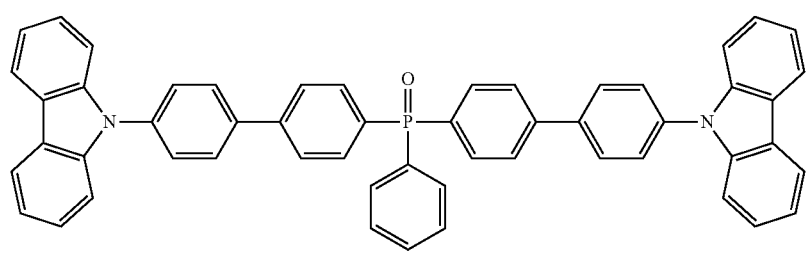

(6)

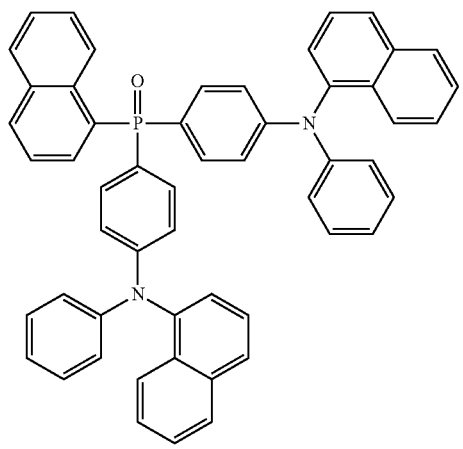 (7)

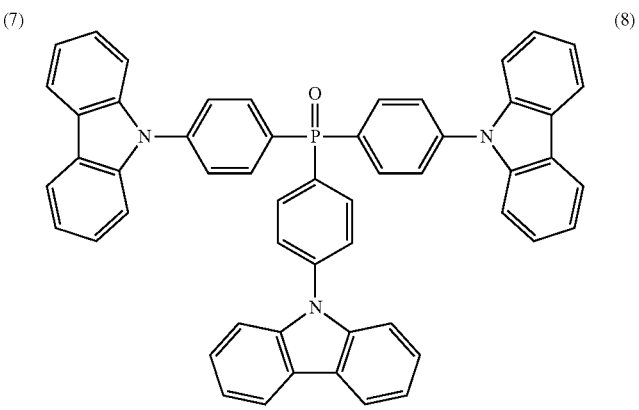 (8)

In the case where any one of these compounds is used as a host material in the phosphorescent light-emitting layer, linking of a diarylamino or carbazolyl group having a hole transport property through an aromatic linking group to the phosphine oxide moiety having an electron transport ability improves the balance of electrical charges in the light-emitting layer; however, the luminous efficiency is not sufficiently high for practical use.

Further, in patent document 9, a phosphine oxide compound (Compound 9) containing heterocycles as substituents is disclosed as a host material.

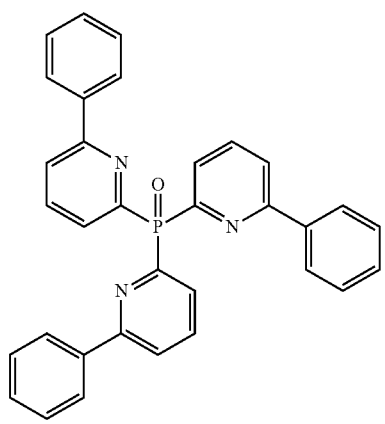 (9)

The aforementioned compound lacks sufficient hole transport ability as it has a good electron transport property but a poor hole transport property. In consequence, the balance of electrical charges in the light-emitting layer is destroyed to reduce the probability of recombination of holes and electrons. For this reason, even if a compound of this kind were used as a phosphorescent host material, high luminous efficiency would not be obtained.

As described above, although trials to utilize phosphine oxide compounds as materials for organic EL devices are disclosed in a number of documents, no phosphorescent host material capable of displaying luminous efficiency and durability of practical level is known yet at the present.

DISCLOSURE OF THE INVENTION

In applications of organic EL devices to display devices such as flat panel displays, it is necessary to improve the luminous efficiency of the device and, at the same time, to fully secure the driving stability of the device. Under the aforementioned circumstances, an object of this invention is to provide an organic EL device that is endowed with such high luminous efficiency and driving stability as to be practically useful and to provide a compound suitable therefor.

The inventors of this invention have found as the result of intensive studies that the use of phosphine oxide compounds of specified structure in organic EL devices can solve the aforementioned problems and completed this invention.

That is, a phosphine oxide compound in which a diarylamine moiety having a hole transport property is directly linked to a nitrogen-containing heterocyclic linking group shows a good balance of electrical charges (holes and electrons) injection/transport properties and an organic EL device containing the said compound is proved to display excellent characteristics.

In addition, the said compound shows good thin-film stability and heat stability and an organic EL device containing the said compound is highly durable and displays excellent driving stability. This invention has been completed on the basis of the aforementioned findings.

This invention relates to an organic electroluminescent device constituted of an anode, organic layers containing a phosphorescent light-emitting layer, and a cathode piled one upon another on a substrate wherein a phosphine oxide derivative represented by the following general formula (1) is contained in at least one layer selected from the group consisting of a phosphorescent light-emitting layer, an electron-transporting layer, a hole-blocking layer, and an exciton-blocking layer.

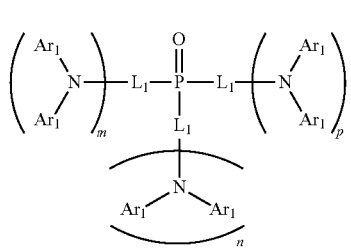
(1)

In general formula (1), $L_1$ is independently a direct bond or an aromatic group with a valence of 1-3 formed by removing 1-3 hydrogen atoms from an aromatic compound represented by the following formula (1a), (1b), or (1c) and at least one of $L_1$s is not a direct bond.

The group $Ar_1$ is independently an aromatic hydrocarbon group of 6-20 carbon atoms or an aromatic heterocyclic group of 3-20 carbon atoms; the two $Ar_1$ groups linked to the same nitrogen atom may join together directly or through another atom to form a nitrogen heterocycle containing the said nitrogen atom and may further form a fused ring together with the said nitrogen heterocycle; the aforementioned aromatic hydrocarbon group or aromatic heterocyclic group may have substituents.

The symbols m, n, and p each is independently an integer of 0-2 and m+n+p is 1-6.

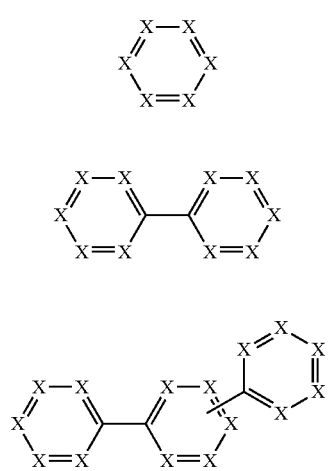

In formula (1a), (1b), or (1c), X is independently a substituted or unsubstituted methine group or nitrogen and, when the aromatic group has a valence of 2 or 3, at least one of Xs is nitrogen. When X is a substituted methine group, the substituent therein is independently an alkyl group of 1-6 carbon atoms, an alkoxyl group of 1-6 carbon atoms, an aryloxyl group of 3-20 carbon atoms, an aromatic hydrocarbon group of 6-20 carbon atoms, or an aromatic heterocyclic group of 3-20 carbon atoms.

Of the phosphine oxide derivatives represented by general formula (1), the ones represented by the following general formula (2) are preferred.

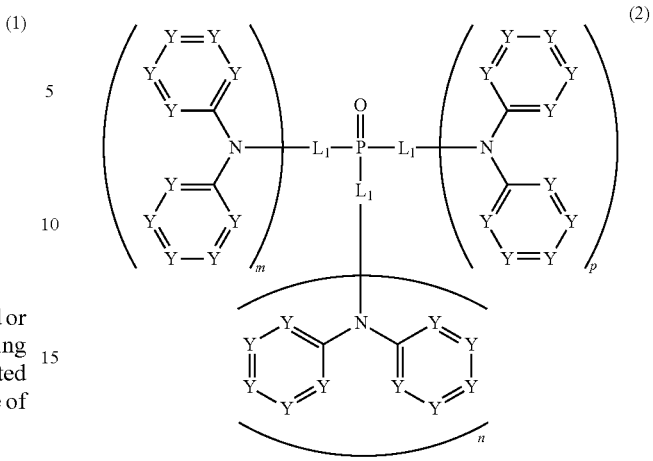
(2)

In general formula (2), Y is independently a substituted or unsubstituted methine group or nitrogen. When Y is a substituted methine group, the substituent therein is independently an alkyl group of 1-6 carbon atoms, an alkoxyl group of 1-6 carbon atoms, an aryloxyl group of 3-20 carbon atoms, an aromatic hydrocarbon group of 6-20 carbon atoms, an aromatic heterocyclic group of 3-20 carbon atoms, or an amino group substituted with an aromatic hydrocarbon group of 6-14 carbon atoms or with an aromatic heterocyclic group of 3-14 carbon atoms. In the case of the substituted amino group, the aromatic hydrocarbon groups or aromatic heterocyclic groups linked to the nitrogen atom of the amino group may join together directly or through another atom to form a nitrogen heterocycle containing the said nitrogen atom and may further form a fused ring together with the said nitrogen heterocycle.

Furthermore, two six-membered aromatic hydrocarbon groups or two six-membered nitrogen-containing aromatic heterocyclic groups existing as substituents on the nitrogen atom that is linked to $L_1$ may join together directly or through another atom to form a nitrogen heterocycle containing the said nitrogen atom that is linked to $L_1$ and may further form a fused ring together with the said nitrogen heterocycle.

The group $L_1$ and the symbols m, n, and p respectively have the same meaning as $L_1$, m, n, and p in general formula (1).

Further, this invention relates to an organic electroluminescent device wherein the organic layer containing the aforementioned phosphine oxide derivative is a light-emitting layer containing a phosphorescent dopant.

BRIEF DESCRIPTION OF THE DRAWING

FIG. 1 schematically illustrates the cross section of an example of an organic EL device.

PREFERRED EMBODIMENTS OF THE INVENTION

An organic electroluminescent device according to this invention comprises a phosphine oxide derivative represented by the aforementioned general formula (1) in its organic layers. The organic layers are disposed between an anode and a cathode and contain a light-emitting layer as an essential layer and may contain other layers according to the need.

A phosphine oxide derivative represented by general formula (1) has a phosphine oxide moiety to which a nitrogen heterocycle having an electron injection/transport ability is linked directly ($L_1$-P=O) and at least one $NAr_1Ar_1$ group having a hole injection/transport ability.

In the aforementioned general formula (1), $L_1$ is independently a direct bond or an aromatic group with a valence of 1-3 formed by removing 1-3 hydrogen atoms from an aromatic compound represented by the aforementioned formula (1a), (1b), or (1c) and at least one of $L_1$s is not a direct bond. Suppose attention is paid to the aforementioned formula (1b) and one of the six-membered rings therein is expressed as A. Then, the aromatic compound represented by formula (1b) can be expressed as $A_1$-$A_2$. In the case where the aforementioned aromatic group is monovalent, the said group is expressed as -$A_1$-$A_2$ and the integer m, n, or p denoting the number of $NAr_1Ar_1$ groups in general formula (1) becomes 0. In the case where the aromatic group is divalent, the said group is expressed as -$A_1$-$A_2$- and m, n, or p becomes 1. In the case of a trivalent aromatic group, the group is expressed as -$A_1$-$A_2$< and m. n, or p becomes 2. At least one of $A_1$ and $A_2$ is a nitrogen-containing aromatic ring in the case where the aromatic group in question is divalent or trivalent.

As $L_1$ is an aromatic group with a valence of 1-3 formed by removing 1-3 hydrogen atoms from an aromatic compound represented by the aforementioned formula (1a), (1b), or (1c), the nature of preferable $L_1$ can be understood better by explanation of the aromatic compounds themselves from which $L_1$ is derived. The aromatic compounds to be described below will furnish examples in the explanation of $L_1$ in terms of the aromatic compounds (aromatic hydrocarbon compounds or aromatic heterocyclic compounds) represented by formula (1a), (1b), or (1c). In each formula, X is a substituted or unsubstituted methine group or nitrogen and at least one of Xs is nitrogen in the case where the aromatic group is divalent or trivalent.

Preferable examples of the aromatic hydrocarbon compounds include benzene, biphenyl, and terphenyl and they may have substituents. A more preferable example is benzene and it may have substituents.

Preferable examples of the nitrogen-containing aromatic hydrocarbon compounds include pyridine, pyrazine, pyrimidine, pyridazine, and triazine and they may have substituents and preferable examples further include 2- or 3-ring compounds which are formed by linking linearly either the cited heterocyclic compounds only or the cited heterocyclic compounds and benzene. More preferable examples include pyridine, pyrazine, pyrimidine, pyridazine, triazine, bipyridine, bipyrimidine, bitriazine, and phenylpyridine and they may have substituents.

In the case where X is a substituted methine group in formula (1a), (1b), or (1c), the substituent therein is independently an alkyl group of 1-6 carbon atoms, an alkoxyl group of 1-6 carbon atoms, an aryloxyl group of 3-20 carbon atoms, an aromatic hydrocarbon group of 6-20 carbon atoms, or an aromatic heterocyclic group of 3-20 carbon atoms.

Examples of the alkyl groups of 1-6 carbon atoms include a methyl group, an ethyl group, a propyl group, an isopropyl group, a butyl group, an isobutyl group, a sec-butyl group, a tert-butyl group, a pentyl group, a hexyl group, and a cyclohexyl group. Examples of the alkoxyl groups of 1-6 carbon atoms include a methoxy group, an ethoxy group, a propoxy group, an isopropoxy group, a butoxy group, an isobutoxy group, a sec-butoxy group, and a tert-butoxy group. Examples of the aryloxyl groups of 3-20 carbon atoms include a phenoxy group, a pyridyloxy group, a pyrazinyloxy group, a pyrimidinyloxy group, a pyridazinyloxy group, and a triazinyloxy group.

Examples of the aromatic hydrocarbon groups of 6-20 carbon atoms include a phenyl group, a biphenylyl group, and a terphenylyl group. Examples of the aromatic heterocyclic groups of 3-20 carbon atoms include the monovalent groups formed by removing one hydrogen atom from thiophene, thiazole, furan, oxazole, pyran, pyrrole, imidazole, pyrazole, isothiazole, isoxazole, furazan, triazole, pyridine, pyrazine, pyrimidine, pyridazine, and triazine or the monovalent groups formed by removing one hydrogen atom from 2- to 4-ring compounds which are formed by linking linearly either the cited heterocyclic compounds only or the cited heterocyclic compounds and benzene.

In general formula (1), $Ar_1$ is an aromatic hydrocarbon group of 6-20 carbon atoms or an aromatic heterocyclic group of 3-20 carbon atoms and may have substituents. Preferable examples of $Ar_1$ include the monovalent groups derived from benzene, pyridine, pyrimidine, triazine, naphthalene, quinoline, isoquinoline, quinoxaline, and naphthyridine. The two $Ar_1$ groups linked to the same nitrogen atom may join together directly or through another atom to form a nitrogen heterocycle containing the said nitrogen atom and may further form a fused ring together with the said nitrogen heterocycle. For example, the nitrogen heterocycle containing the said nitrogen atom forms a fused ring consisting of 3 or more rings together with the two $Ar_1$ groups. In the case where the two $Ar_1$ groups join together through another atom, examples of the atom include carbon, nitrogen, oxygen, and sulfur and carbon and oxygen are preferred. Moreover, in the case where the two $Ar_1$ groups join directly or through another atom and form a nitrogen heterocycle together with the nitrogen, the said nitrogen heterocycle is preferably five- or six-membered and the fused ring in question has a structure of a five- or six-membered nitrogen heterocycle to which two aromatic rings derived from the two $Ar_1$ groups are fused. That is, it is preferable that the two aromatic hydrocarbon groups or aromatic heterocyclic groups linked to the same nitrogen atom form a nitrogen heterocycle containing the said nitrogen atom and further form a fused ring consisting of 3 or more rings inclusive of the aromatic hydrocarbon rings or aromatic heterocyclic rings. Preferable examples of such fused rings include a carbazole ring, an acridine ring, a phenoxazine ring, and a benzocarbazole ring and a carbazole ring is preferred.

In the case where the aforementioned aromatic hydrocarbon groups or aromatic heterocyclic groups have substituents, preferable examples of substituents include an alkyl group of 1-6 carbon atoms, an alkoxyl group of 1-6 carbon atoms, an aryloxyl group of 3-20 carbon atoms, an aromatic hydrocarbon group of 6-20 carbon atoms, an aromatic heterocyclic group of 3-20 carbon atoms, and an amino group substituted with aromatic hydrocarbon groups of 6-14 carbon atoms or with aromatic heterocyclic groups of 3-14 carbon atoms. The aromatic hydrocarbon groups or aromatic heterocyclic groups linked to the nitrogen atom of the said amino group may join together directly or through another atom to form a nitrogen heterocycle containing the said nitrogen atom and may further form a fused ring together with the said nitrogen heterocycle.

In explanation of the aforementioned substituents of $Ar_1$, those aromatic hydrocarbon groups and aromatic heterocyclic groups which are described in explanation of the substituents in the case where X in $L_1$ is a substituted methine group are cited as preferable examples of the aromatic hydrocarbon groups and aromatic heterocyclic groups here.

In general formula (1), m, n, and p each is independently an integer of 0-2 and m+n+p is 1-6.

As the compounds represented by the aforementioned general formula (2) are included in the compounds represented by general formula (1), they are understood to be preferable compounds. General formula (2) differs from general formula (1) in that Ar₁ is limited to a six-membered aromatic ring; however, L₁, m, n, and p in general formula (2) respectively have the same meaning as L₁, m, n, and p in general formula (1).

In the aforementioned general formula (2), Y is independently a substituted or unsubstituted methine group or nitrogen. In the case where Y is a substituted methine group, the substituent therein is independently an alkyl group of 1-6 carbon atoms, an alkoxyl group of 1-6 carbon atoms, an aryloxyl group of 3-20 carbon atoms, an aromatic hydrocarbon group of 6-20 carbon atoms, an aromatic heterocyclic group of 3-20 carbon atoms, and an amino group substituted with aromatic hydrocarbon groups of 6-14 carbon atoms or with aromatic heterocyclic groups of 3-14 carbon atoms. The aromatic hydrocarbon groups or aromatic heterocyclic groups linked to the nitrogen atom of the said amino group may join together directly or through another atom to form a nitrogen heterocycle containing the said nitrogen atom and may further form a fused ring together with the said nitrogen heterocycle. Further, the two six-membered rings existing as substituents on the nitrogen atom that is linked to L₁ may join together directly or through another atom to form a nitrogen heterocycle containing the said nitrogen atom that is linked to L₁ and may further form a fused ring together with the said nitrogen heterocycle. The situation here is the same as the case where the two Ar₁ groups form a fused ring consisting of 3 or more rings together with the nitrogen heterocycle in general formula (1).

Examples of the phosphine oxide derivatives represented by general formula (1) are illustrated below, but the materials useful for the organic EL devices of this invention are not limited to these examples. The number assigned to the chemical formula is the compound number.

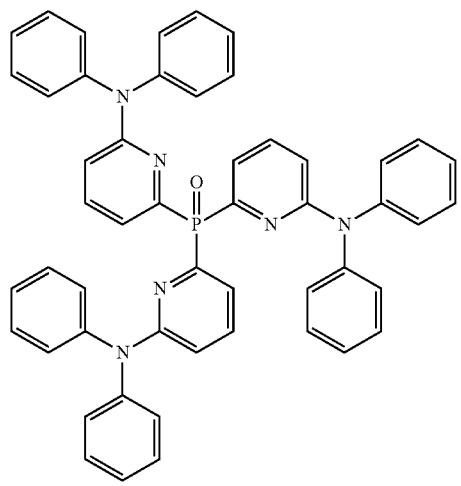

(10)

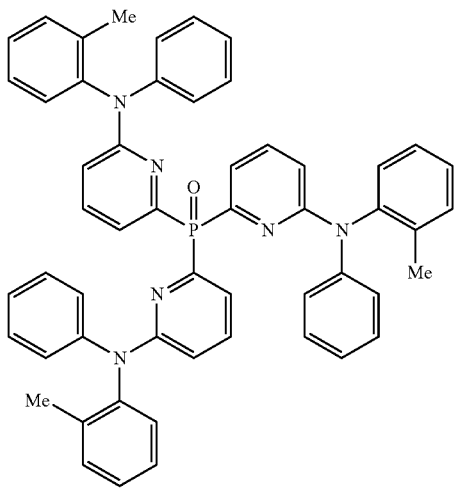

(11)

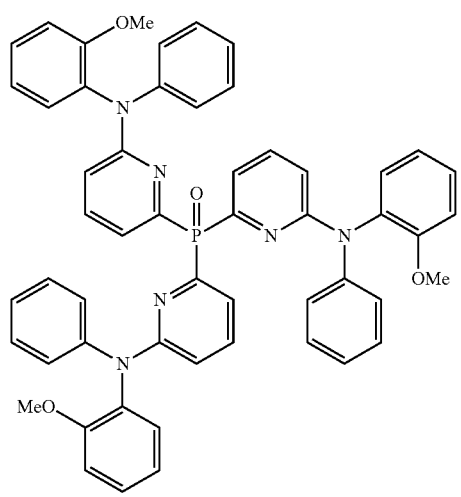

(12)

-continued
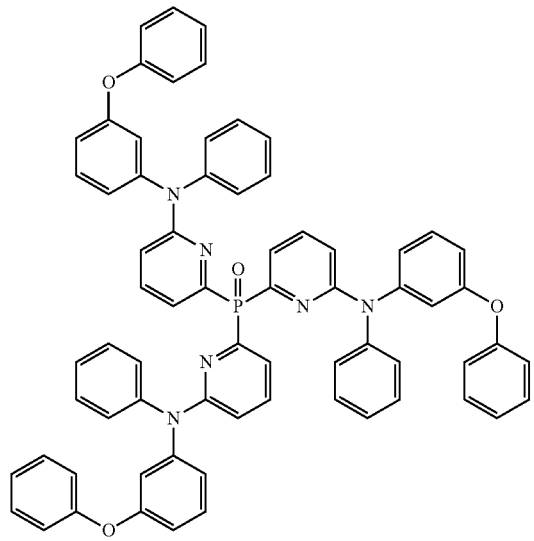
(13)
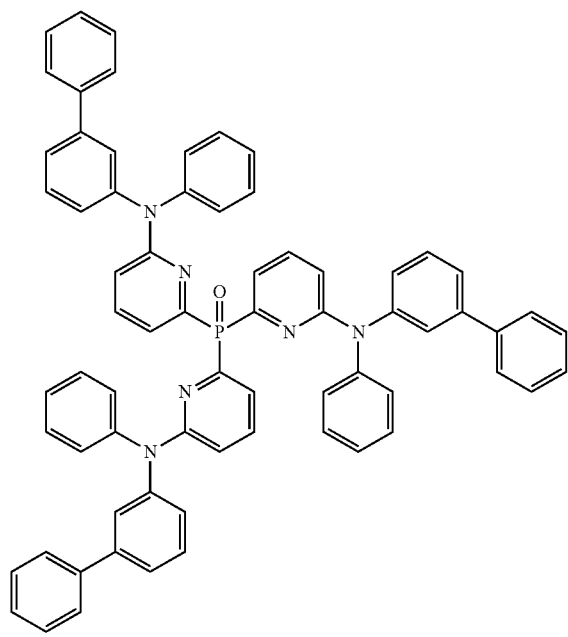
(14)
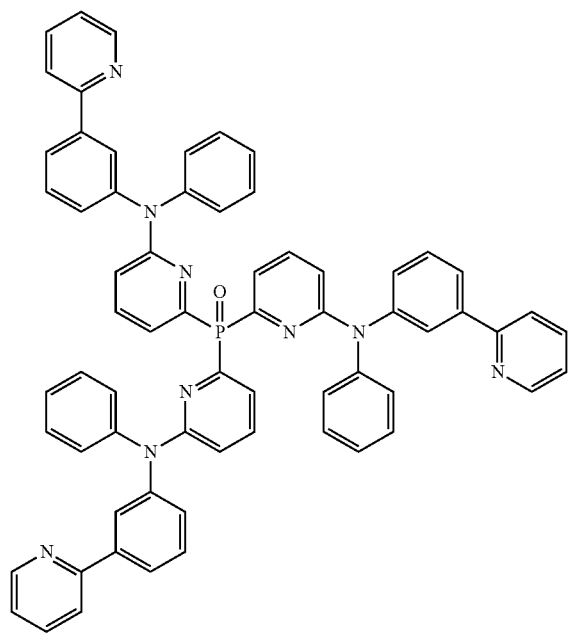
(15)

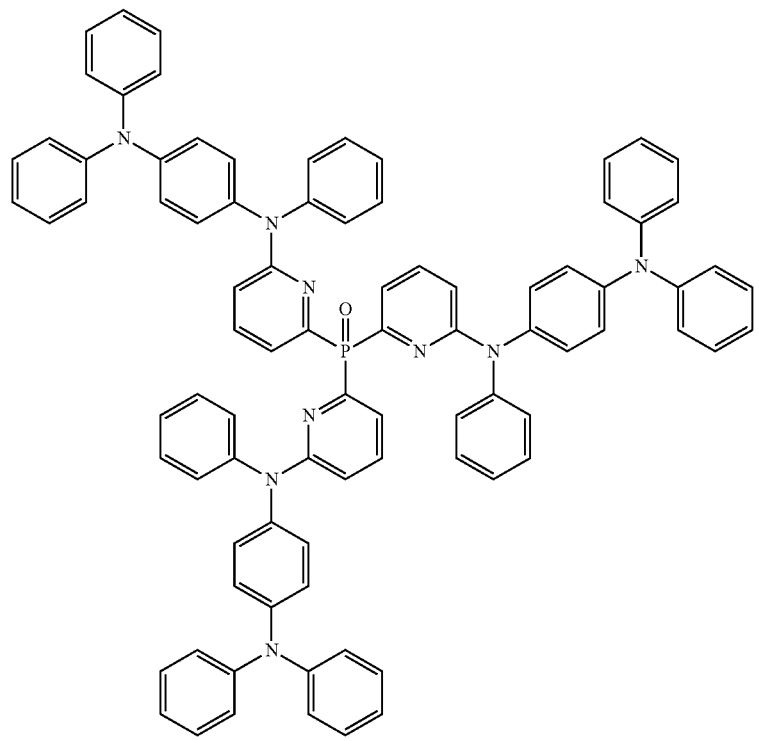
(16)
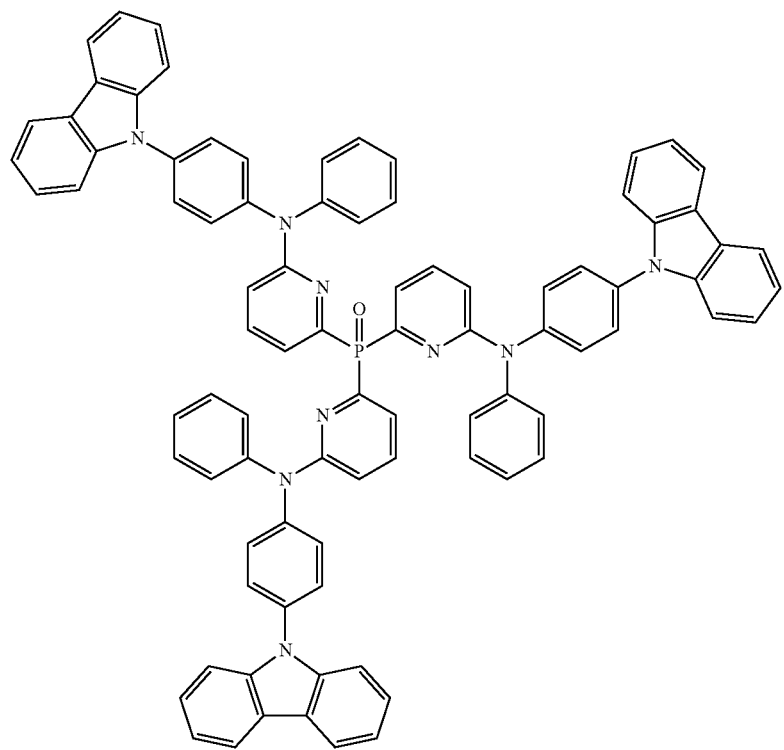
(17)

-continued
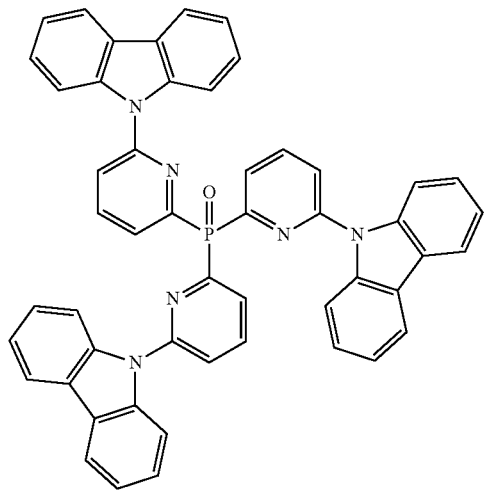
(18)
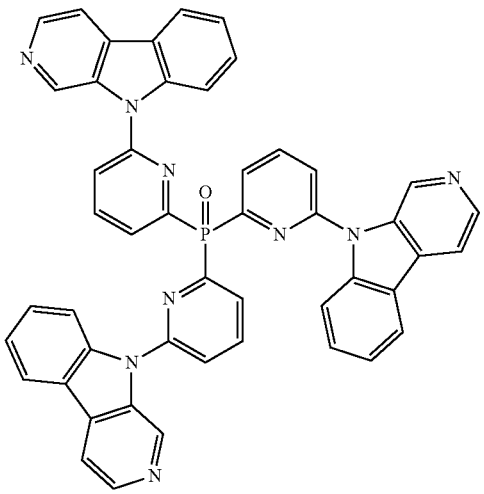
(19)
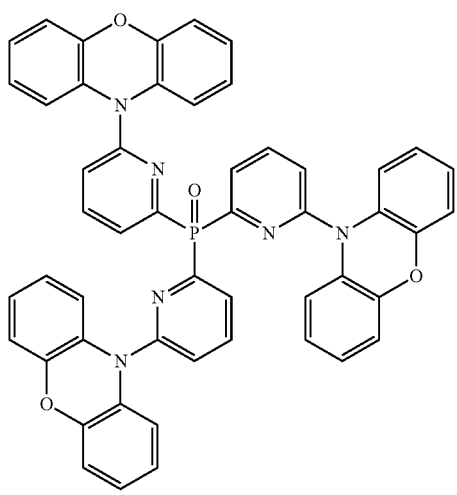
(20)
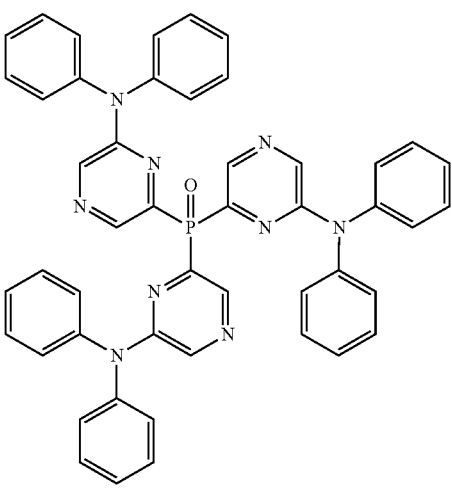
(21)
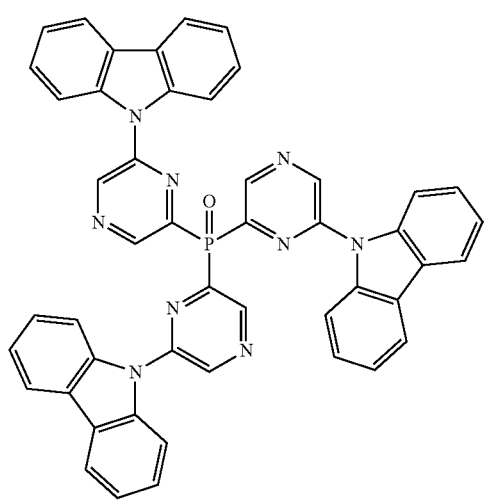
(22)
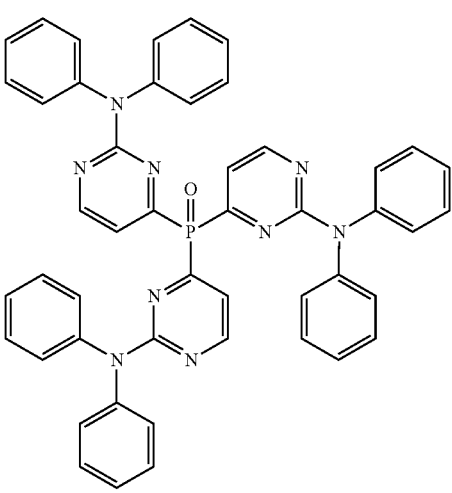
(23)

-continued
(24)
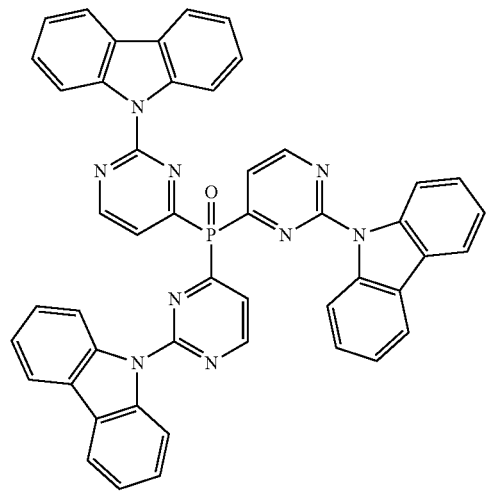
(25)
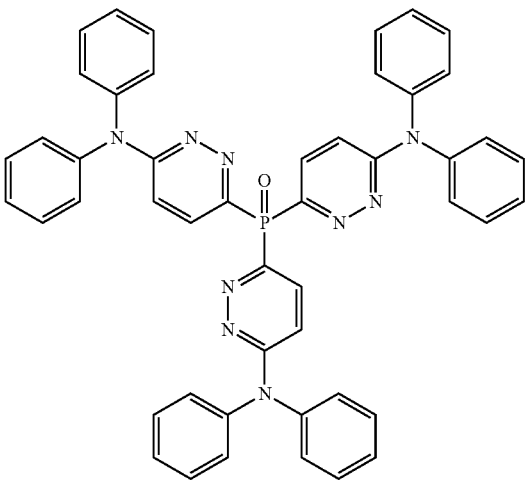
(26)
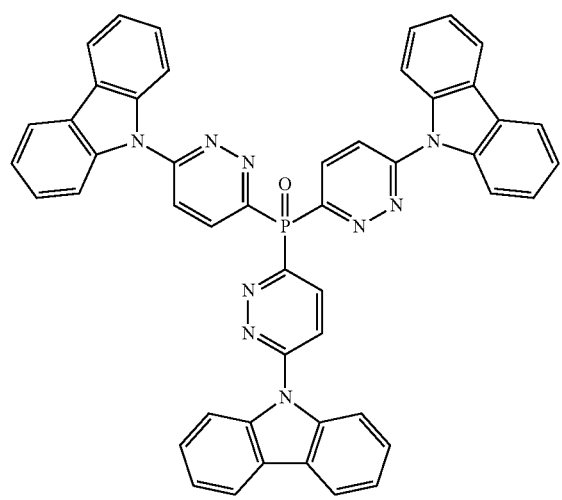
(27)
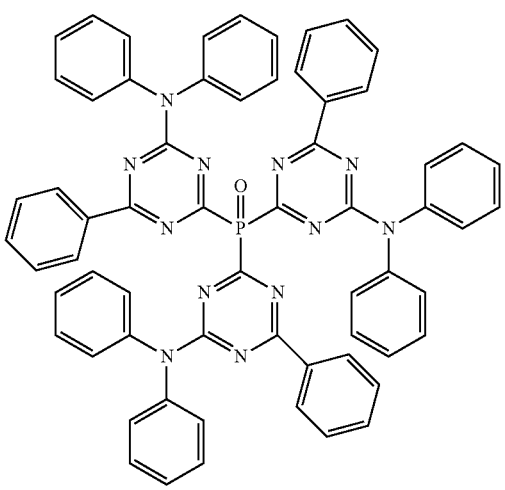
(28)
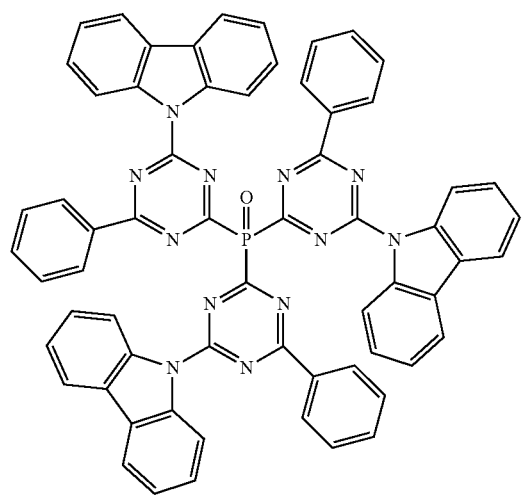

-continued
(29)
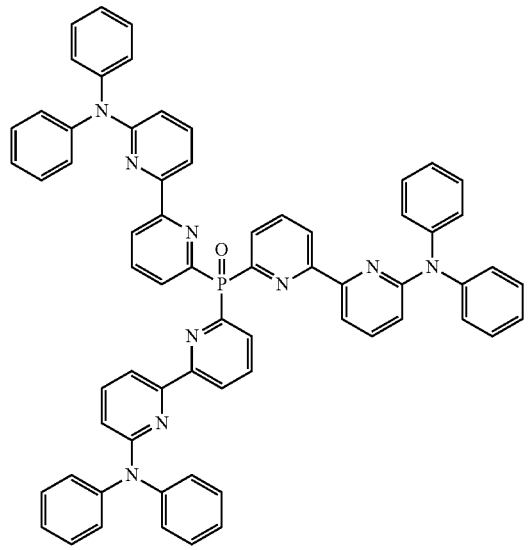
(30)
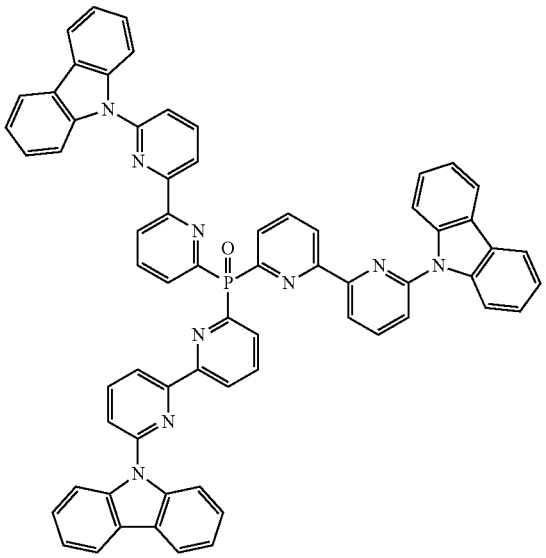
(31)
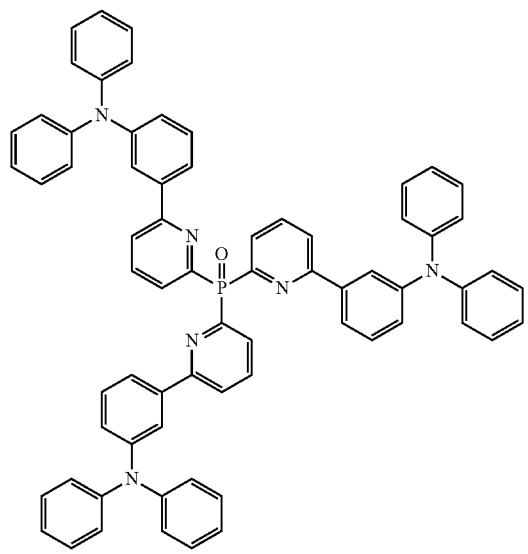
(32)
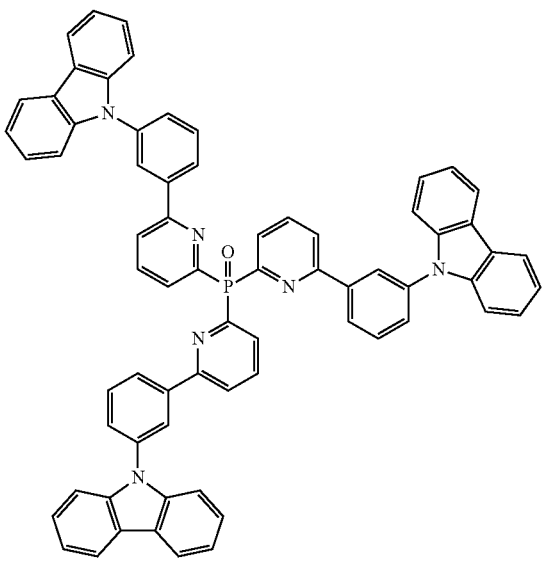
(33)
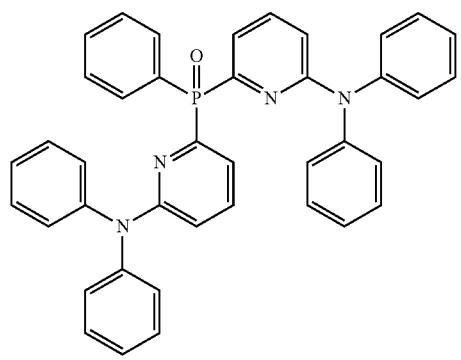

-continued
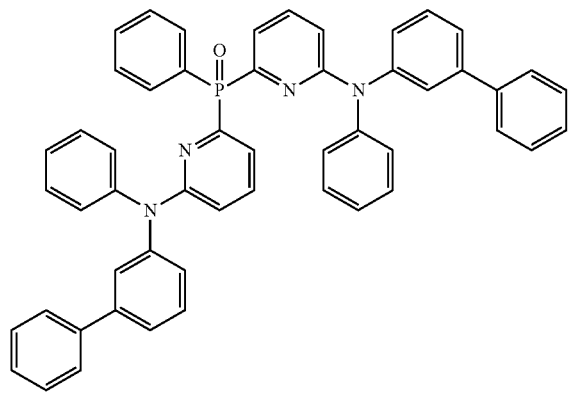
(34)
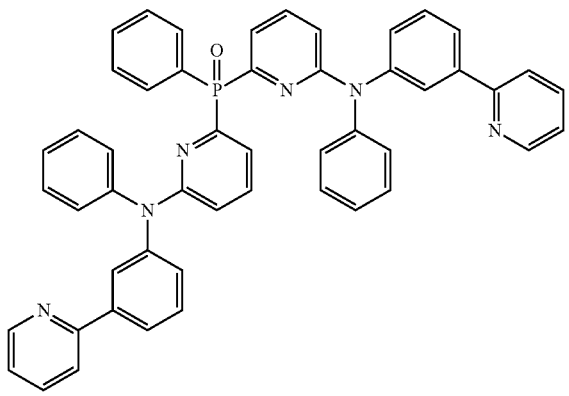
(35)
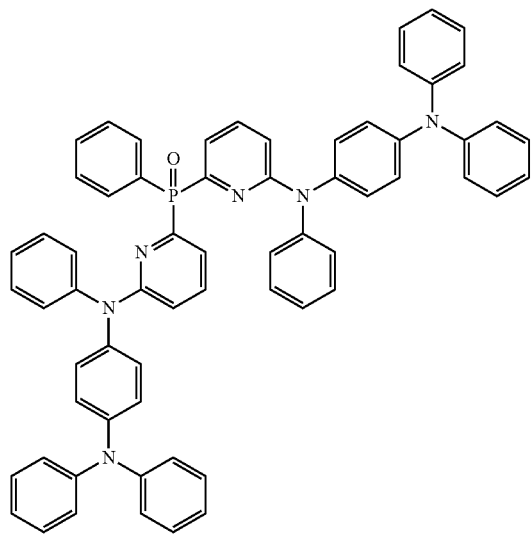
(36)
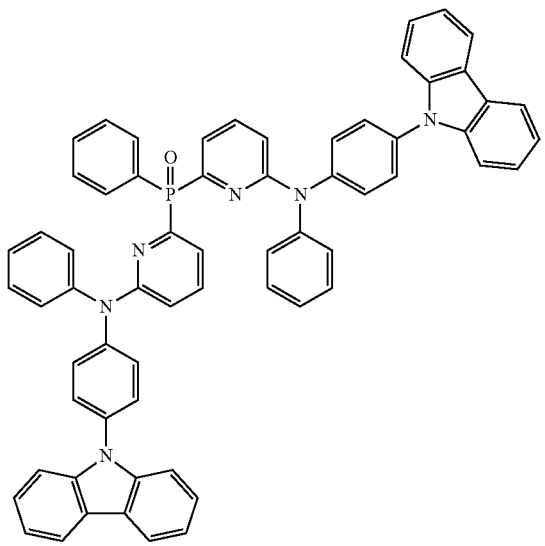
(37)
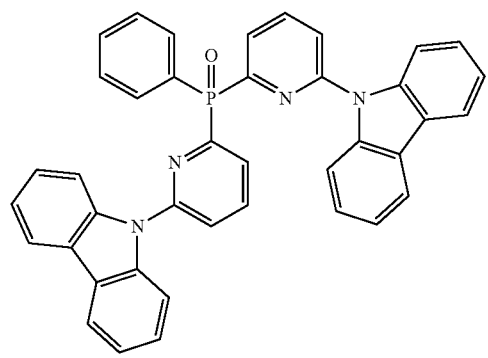
(38)
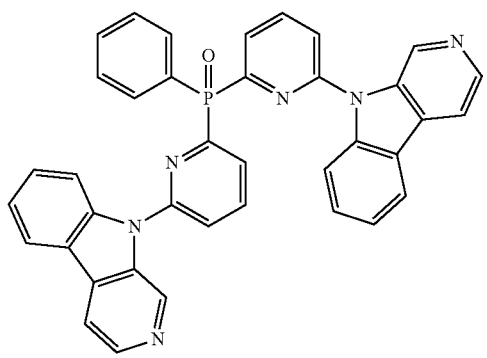
(39)

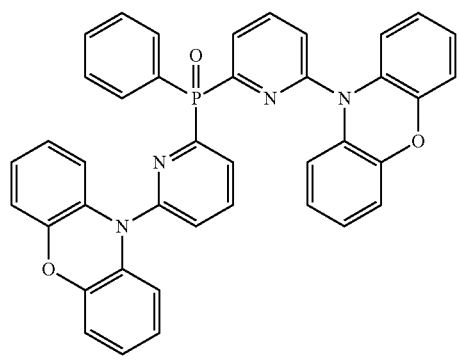
(40)
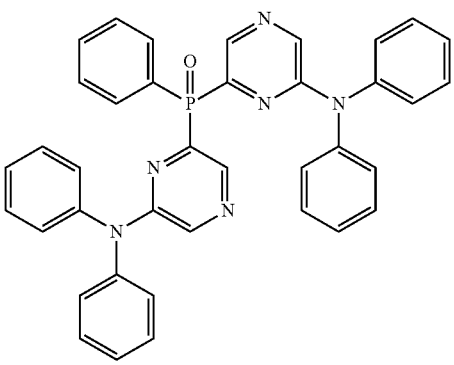
(41)
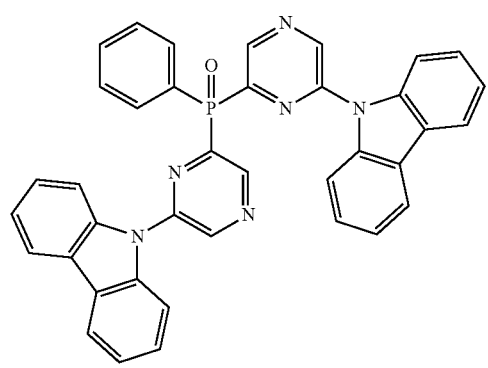
(42)
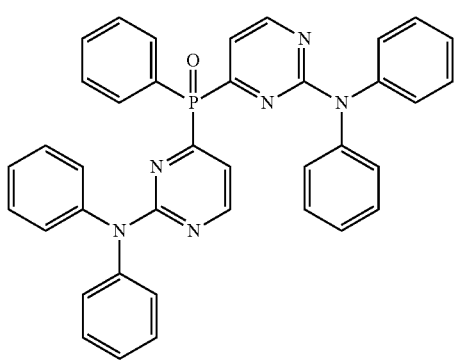
(43)
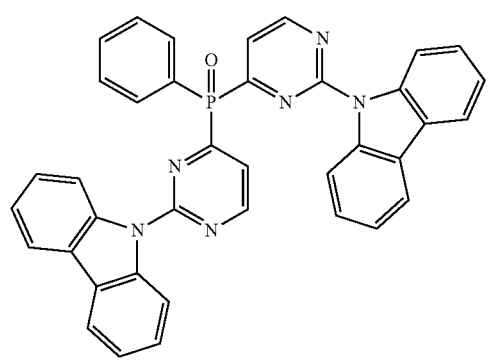
(44)
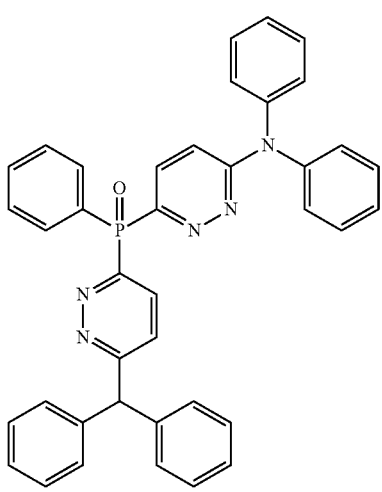
(45)

(46)
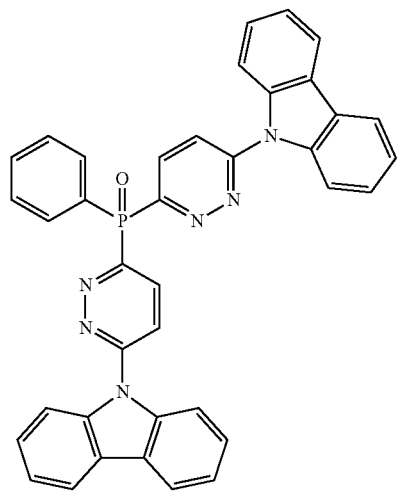
(47)
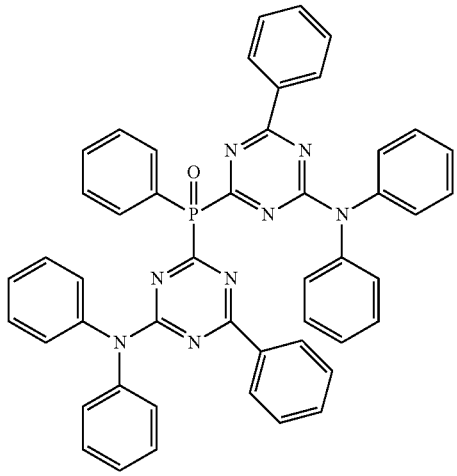
(48)
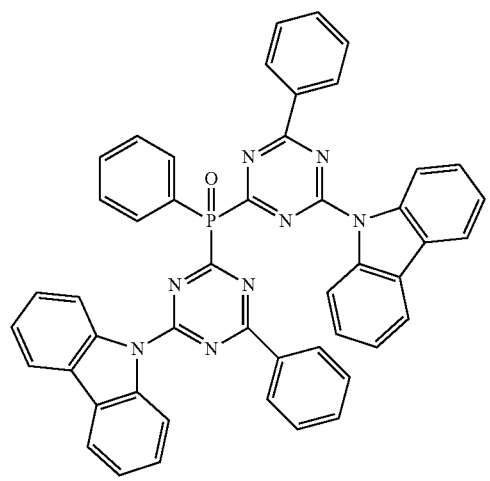
(49)
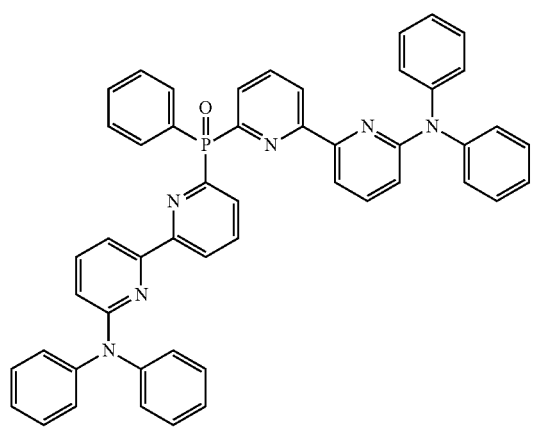

-continued
(50)
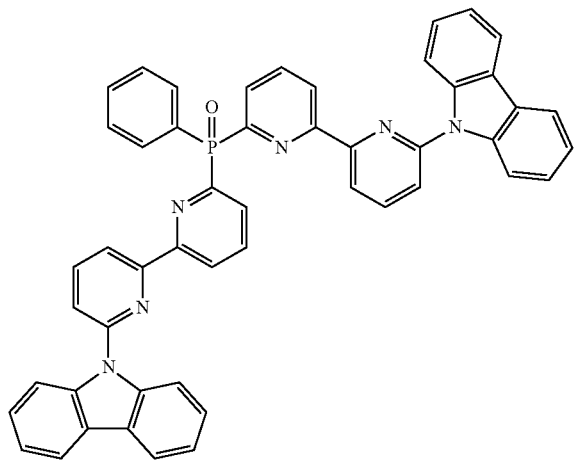
(51)
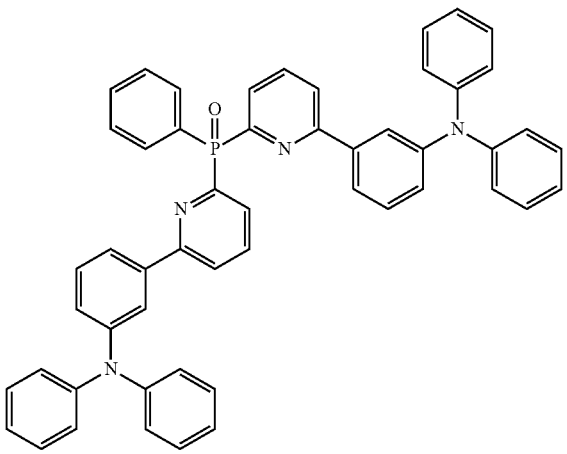
(52)
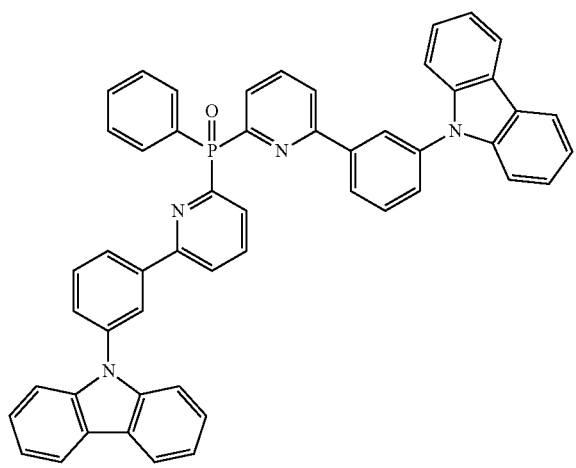
(53)
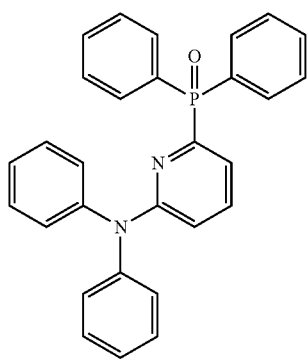
(54)
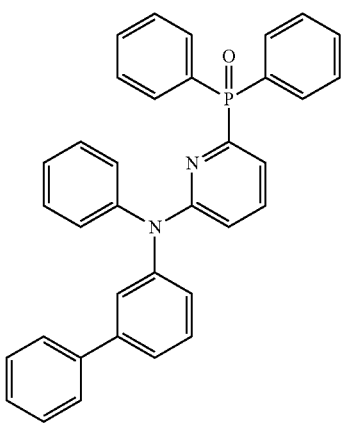

-continued
(55)
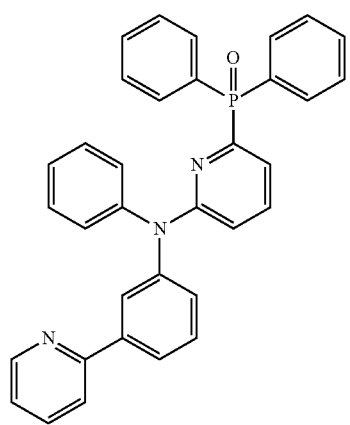
(56)
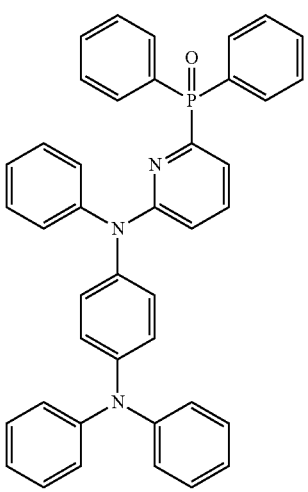
(57)
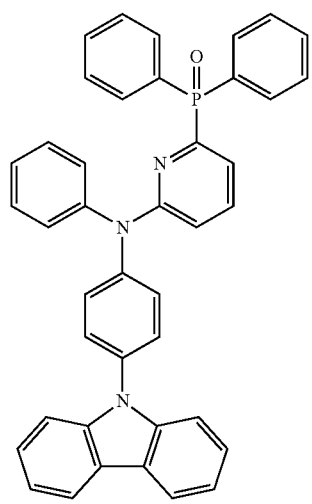
(58)
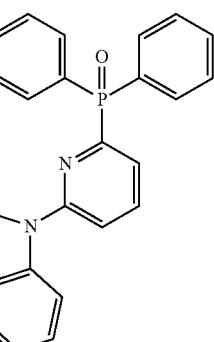
(59)
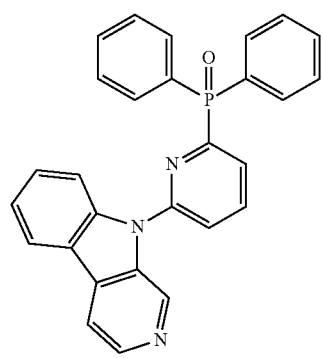
(60)
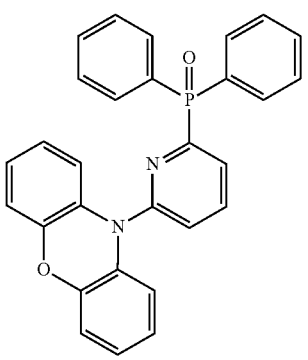

-continued
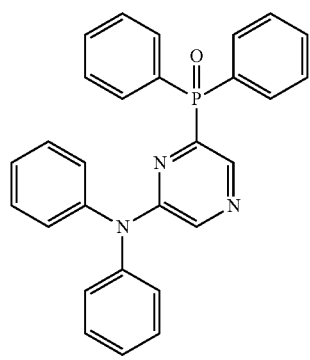
(61)
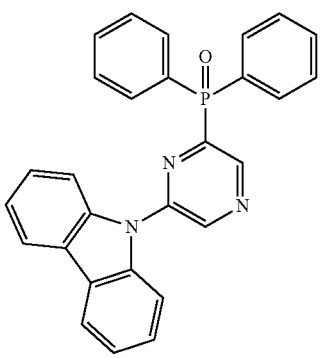
(62)
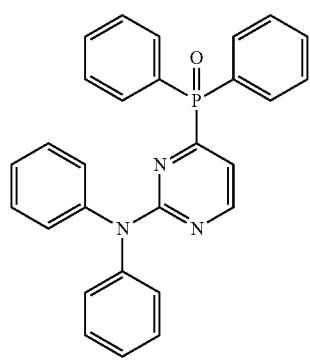
(63)
(64)
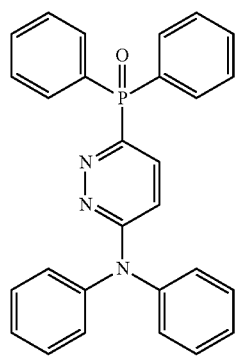
(65)
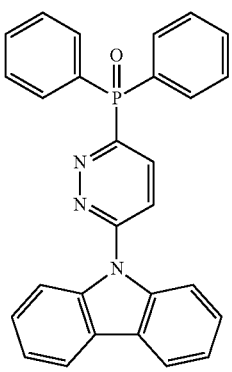
(66)
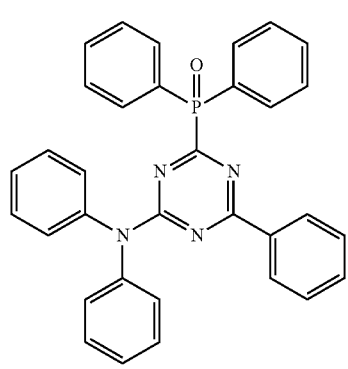
(67)
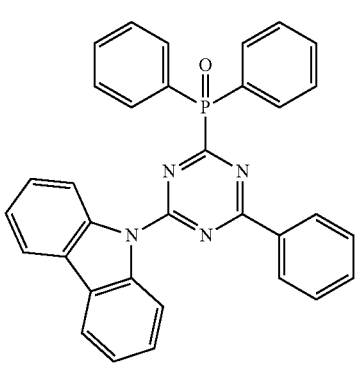
(68)

-continued
(69)
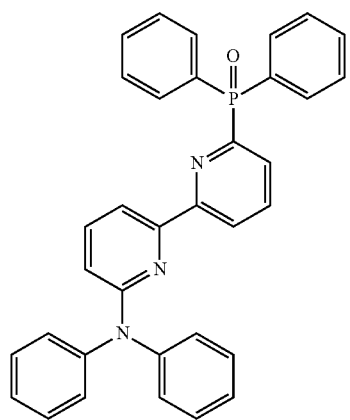
(70)
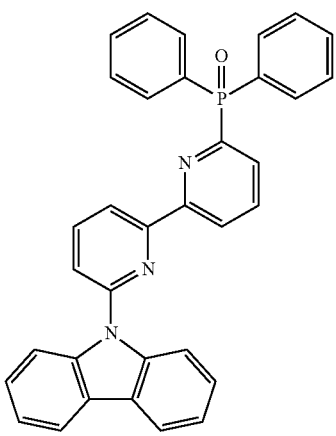
(71)
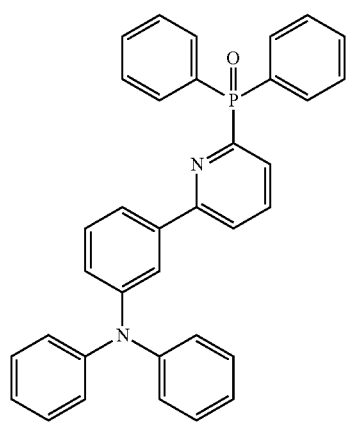
(72)
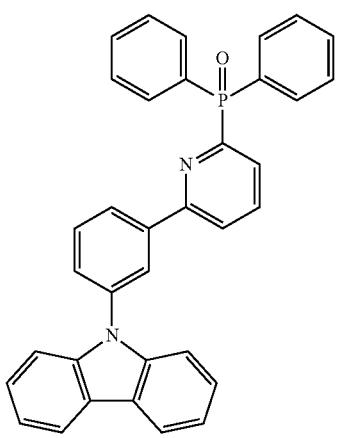
(73)
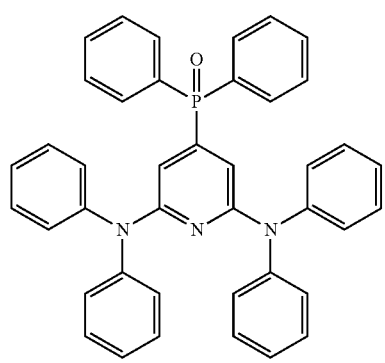
(74)
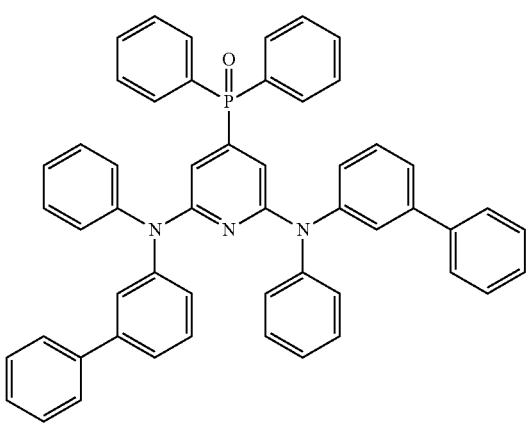

-continued
(75)
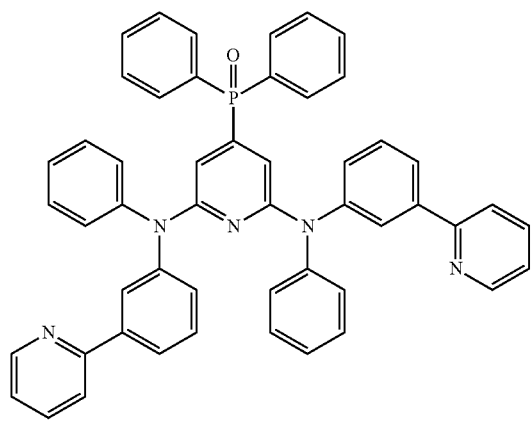
(76)
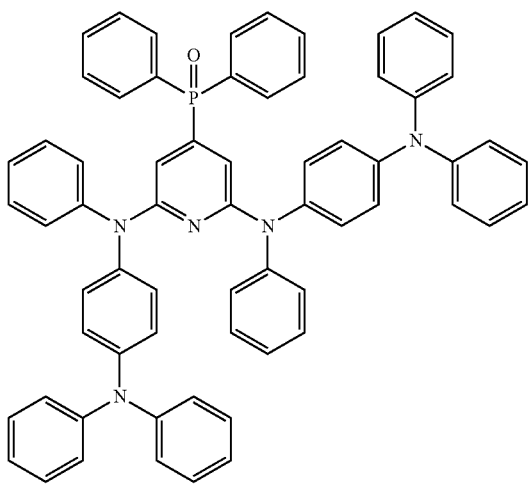
(77)
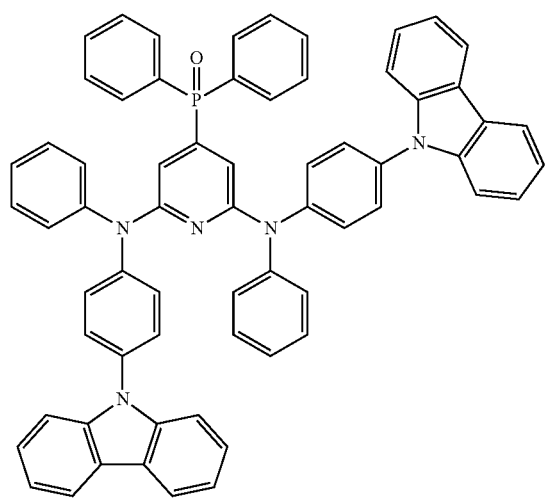
(78)
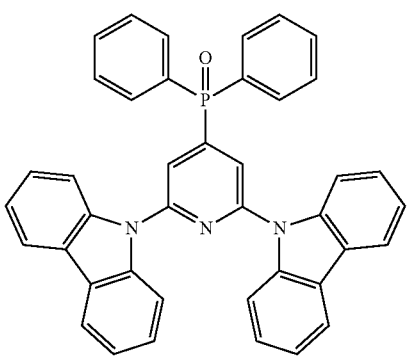
(79)
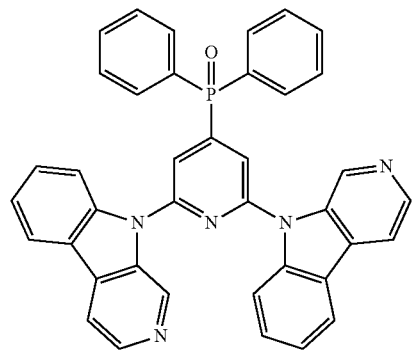
(80)
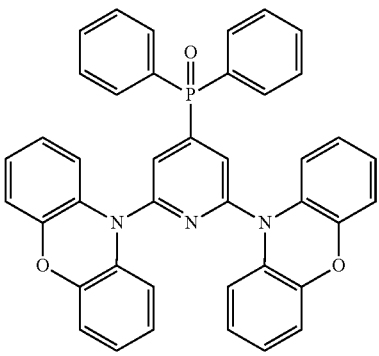

-continued
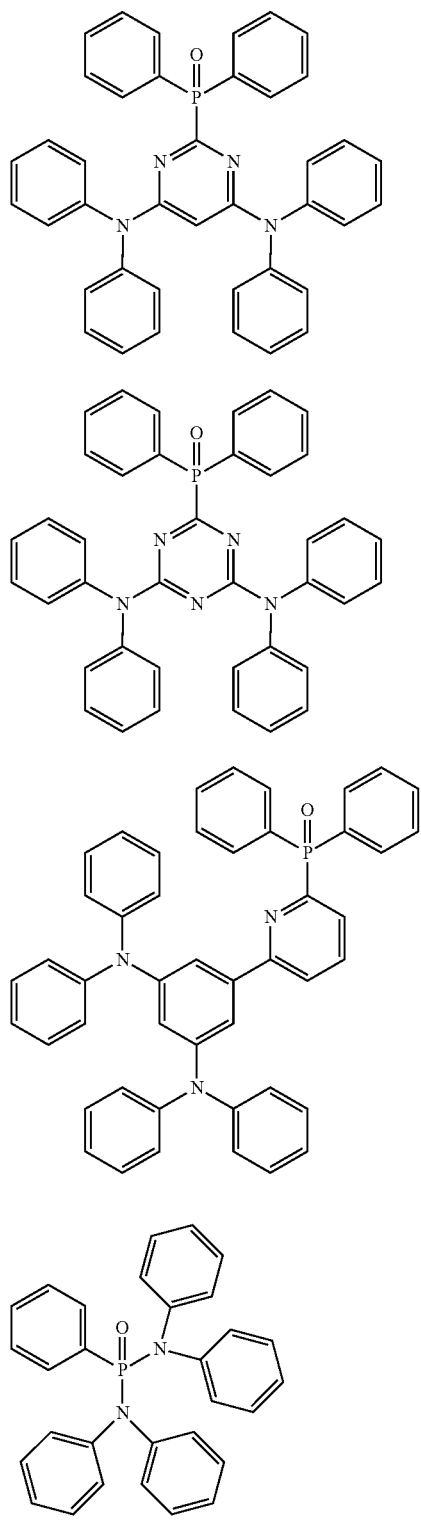
(81)
(83)
(85)
(87)
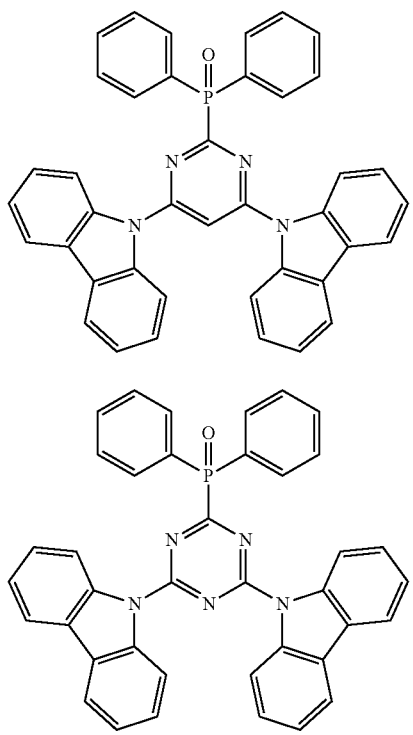
(82)
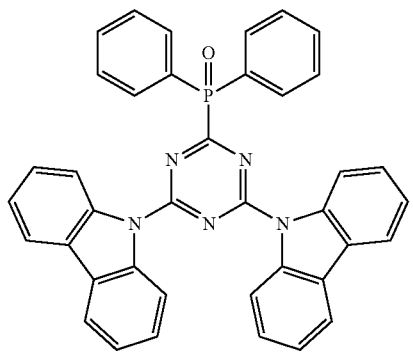
(84)
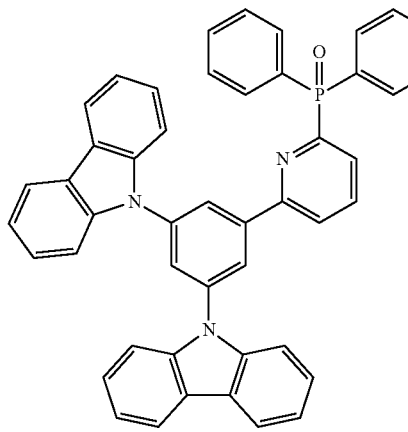
(86)
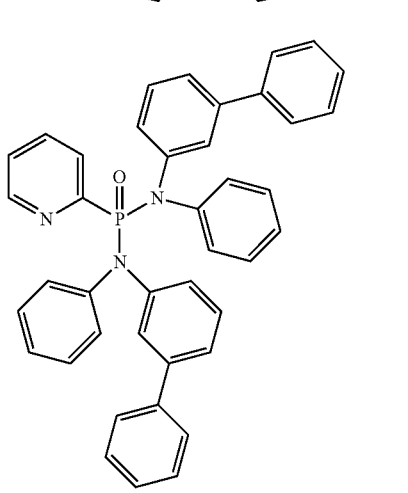
(88)

-continued
(89)
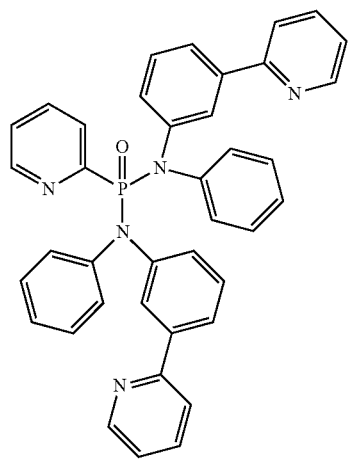
(90)
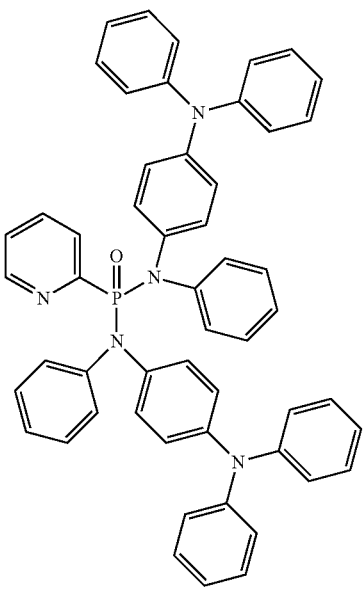
(91)
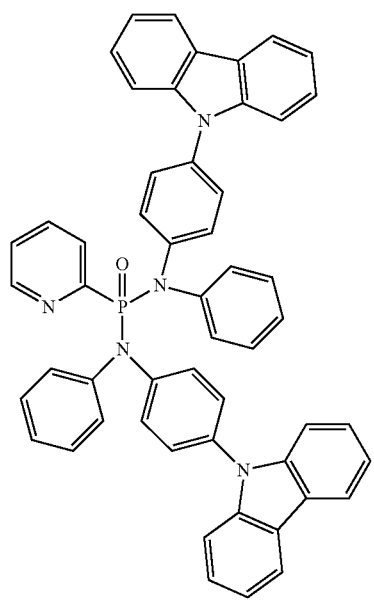
(92)
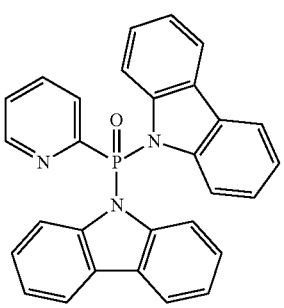
(93)
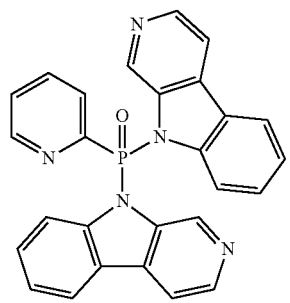
(94)
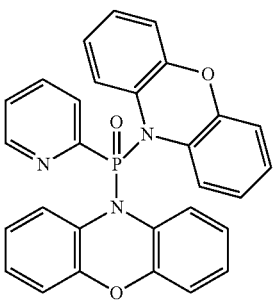

-continued
(95)
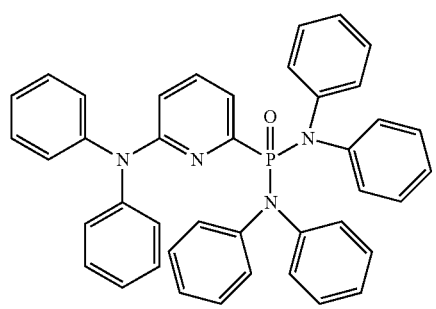
(96)
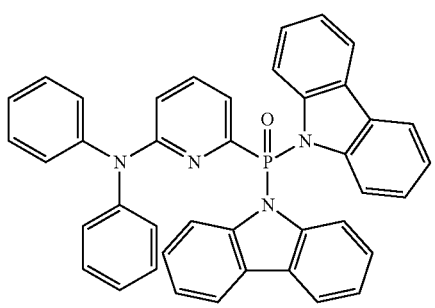
(97)
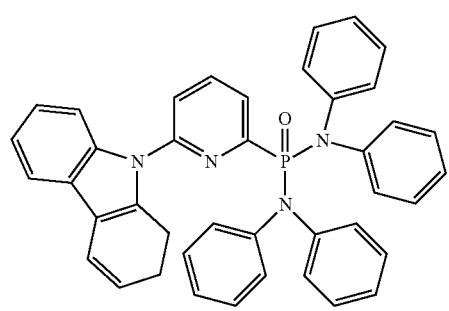
(98)
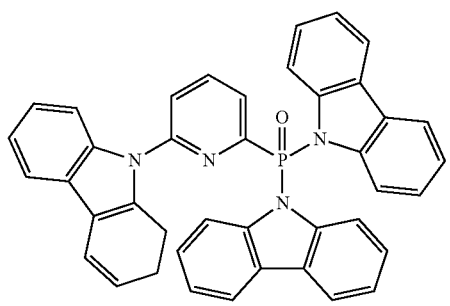
(99)
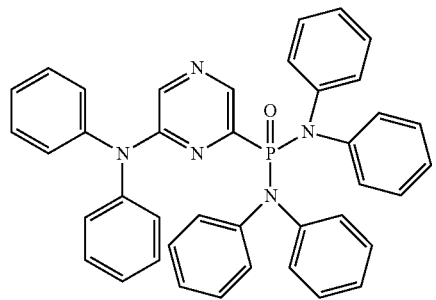
(100)
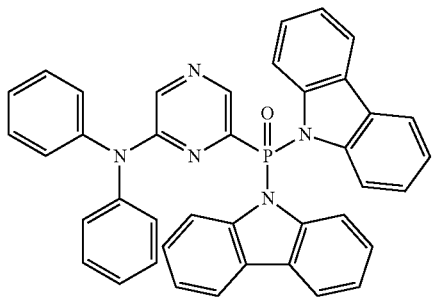
(101)
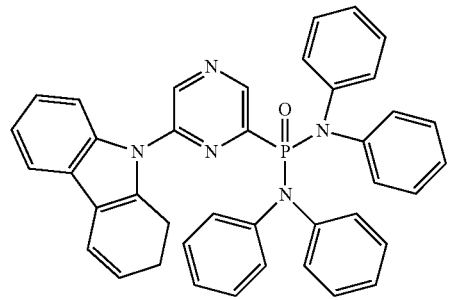
(102)
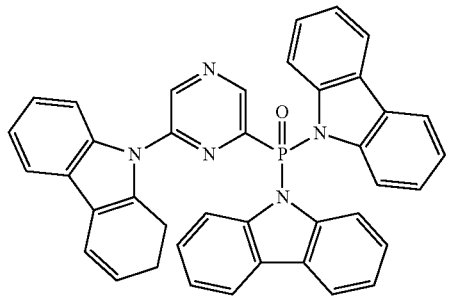
(103)
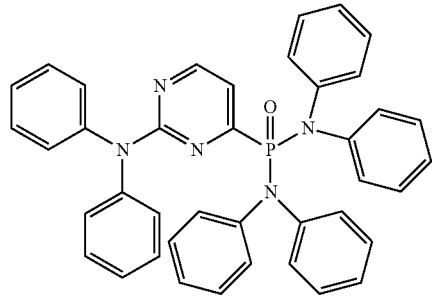
(104)
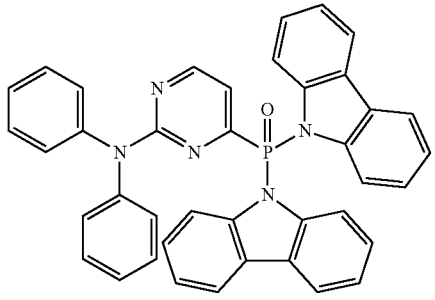

-continued
(105)
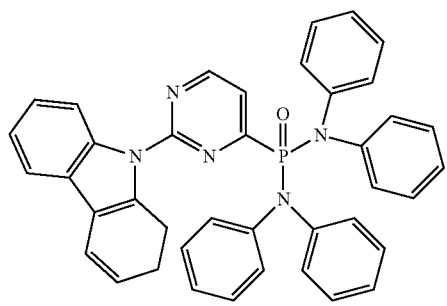
(106)
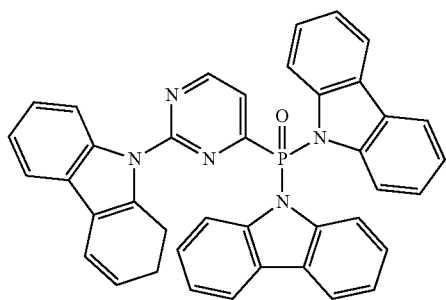
(107)
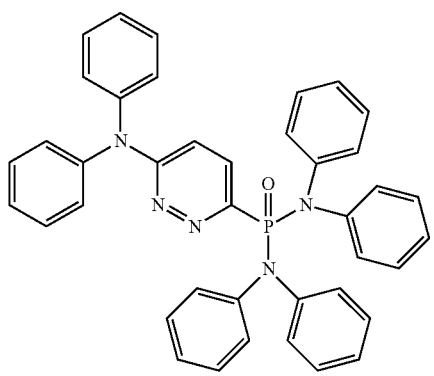
(108)
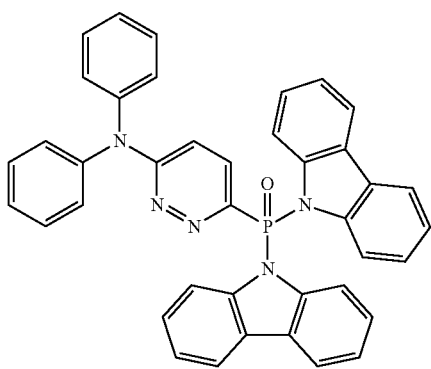
(109)
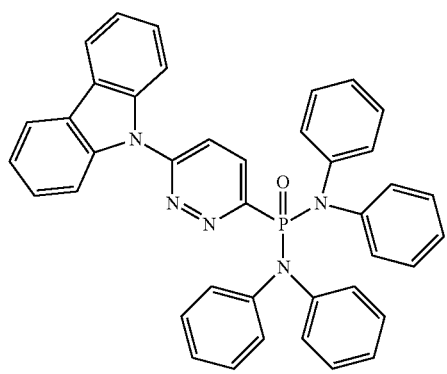
(110)
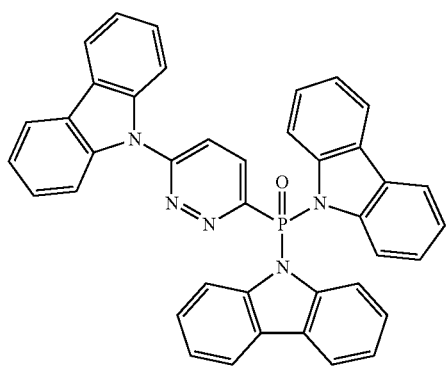
(111)
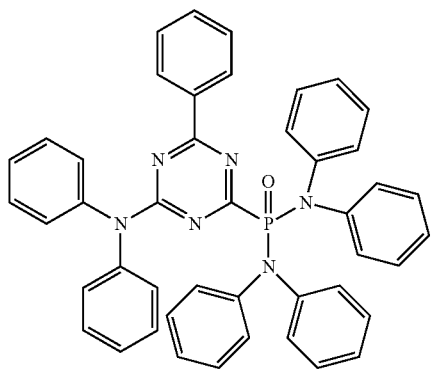
(112)
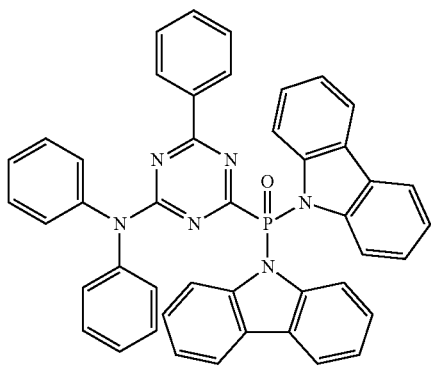

-continued
(113)
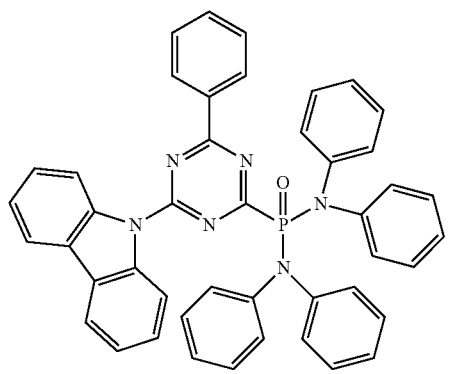
(114)
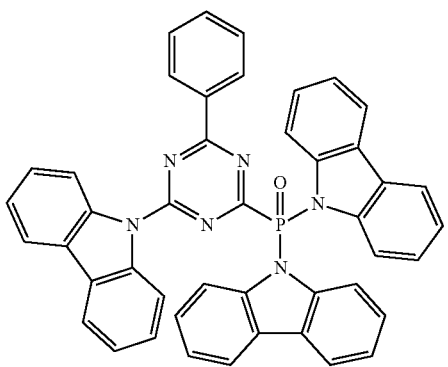
(115)
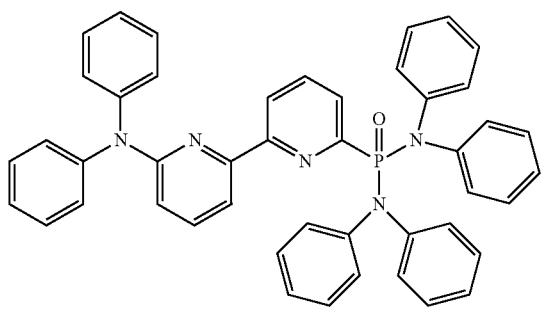
(116)
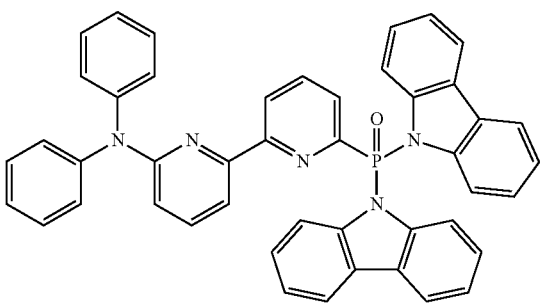
(117)
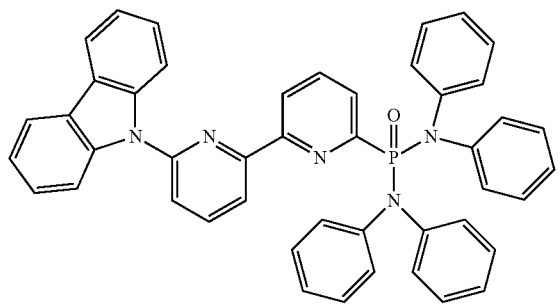
(118)
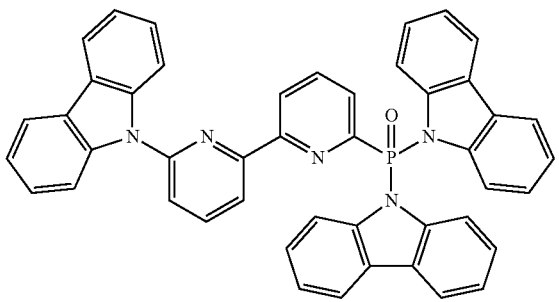
(119)
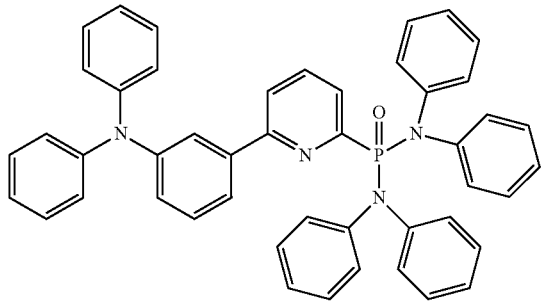
(120)
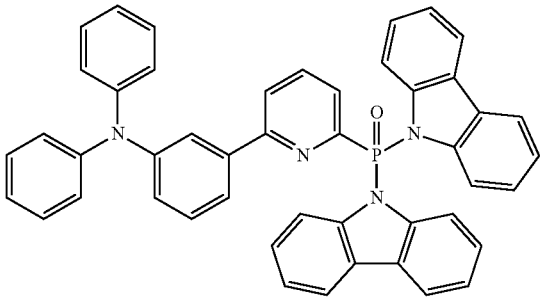

-continued
(121)
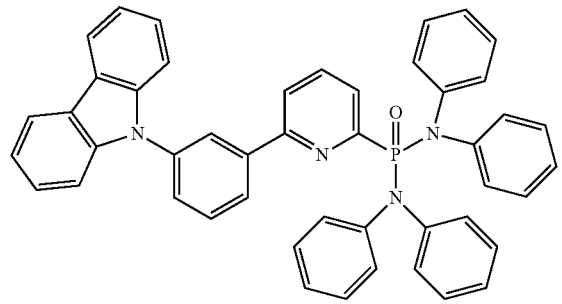
(122)
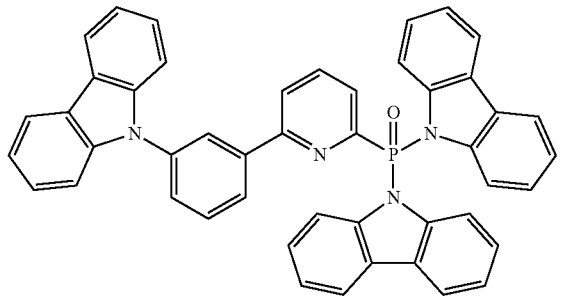
(123)
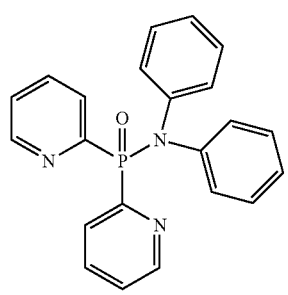
(124)
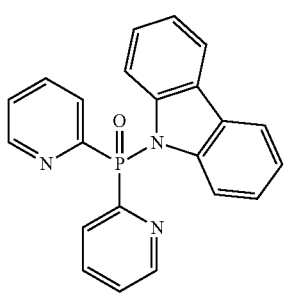
(125)
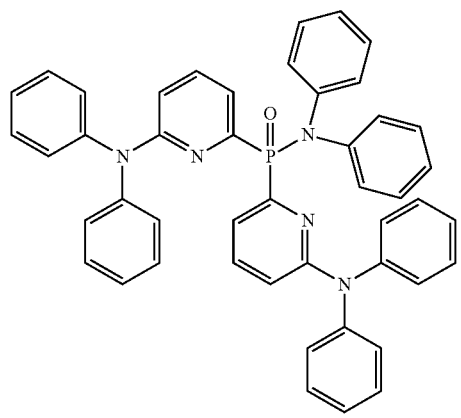
(126)
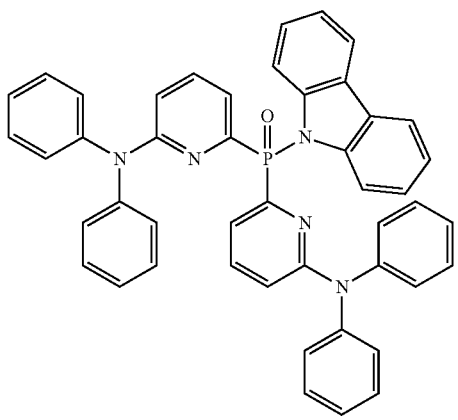
(127)
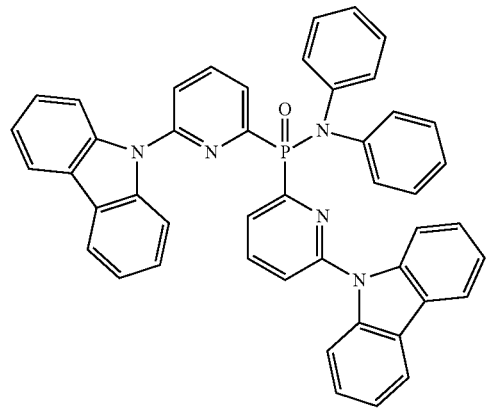
(128)
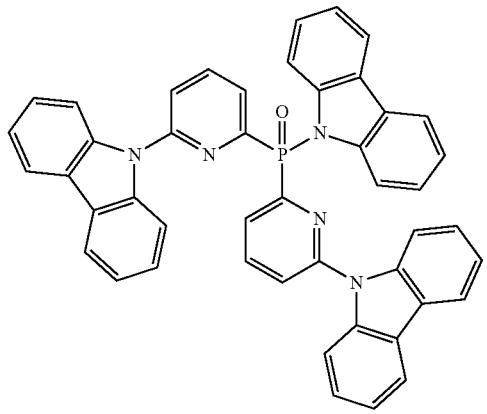

(129)
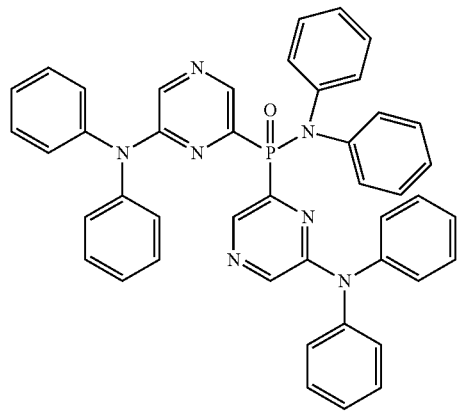
(130)
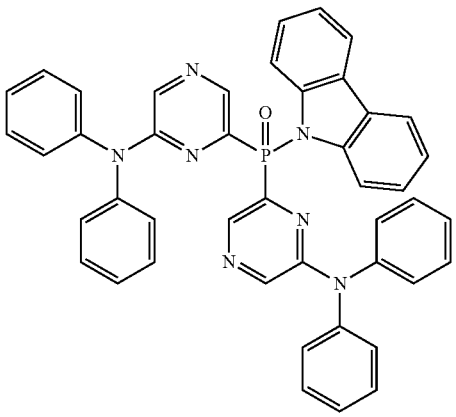
(131)
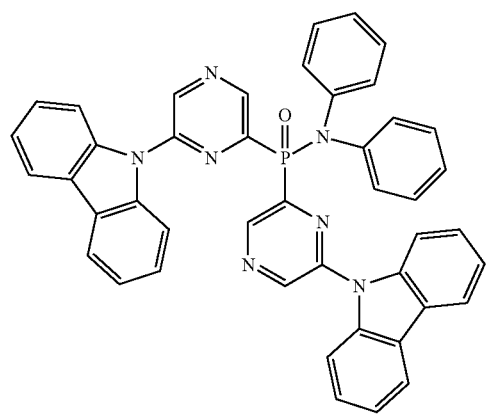
(132)
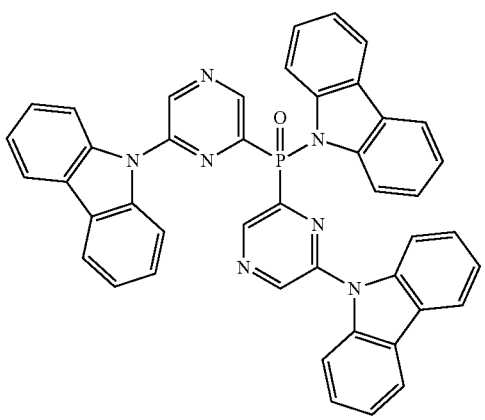
(133)
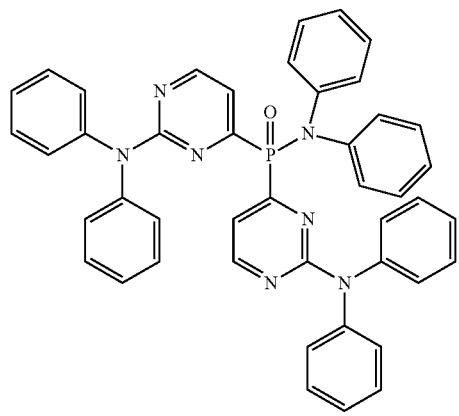
(134)
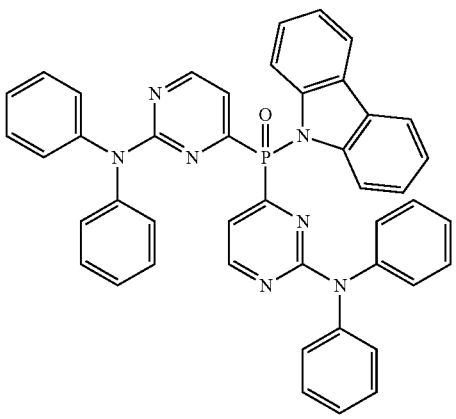

-continued
(135)
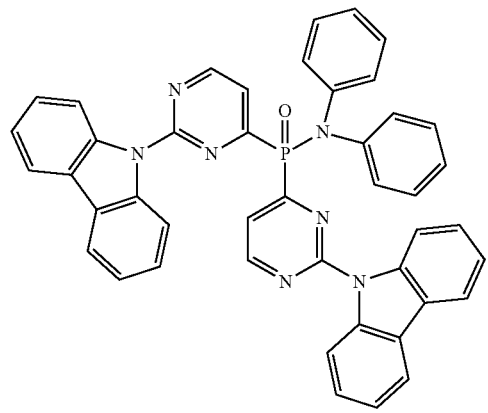
(136)
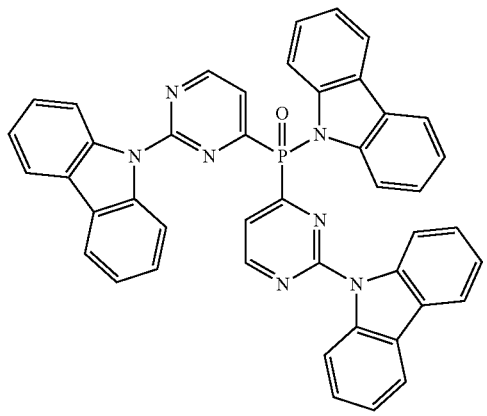
(137)
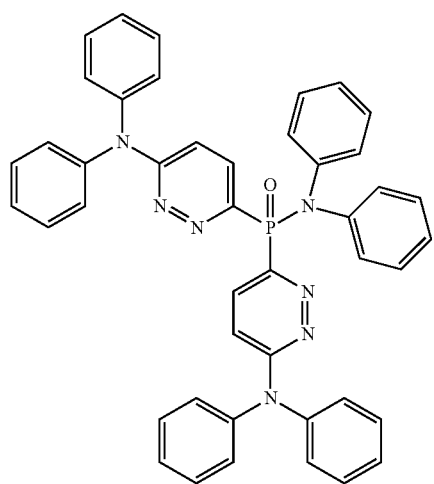
(138)
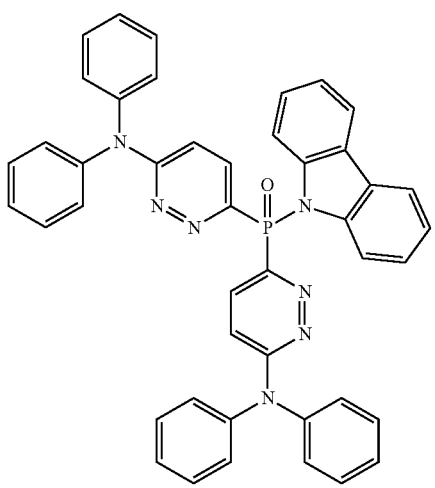
(139)
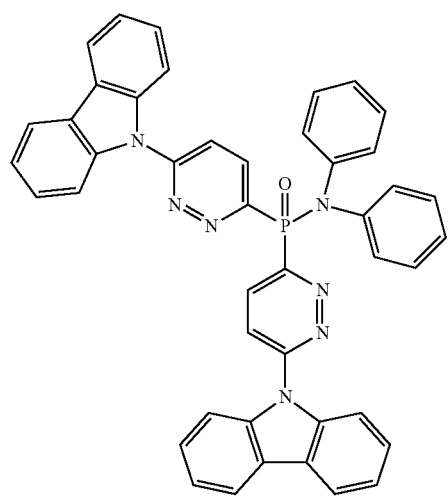
(140)
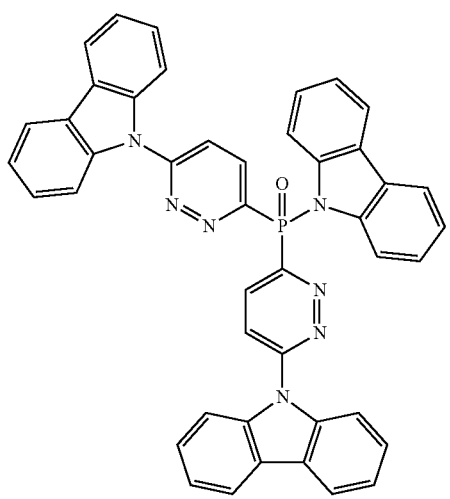

-continued
(141)
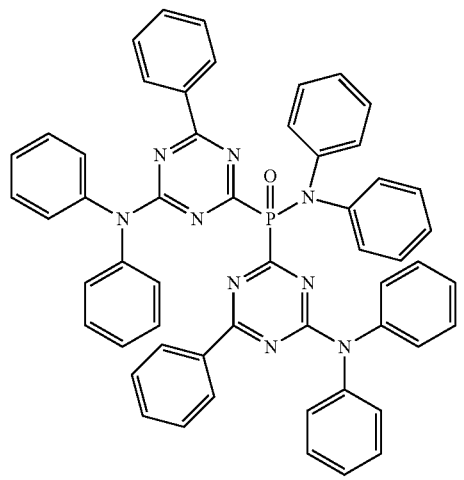
(142)
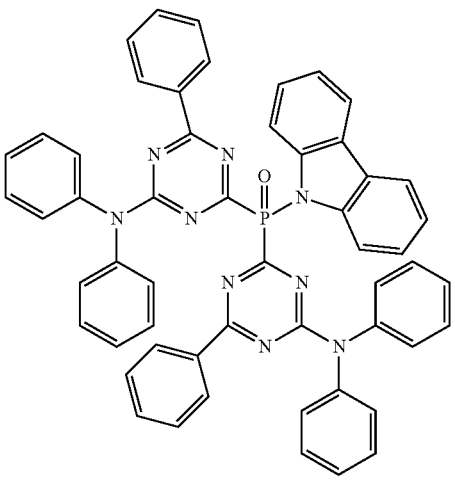
(143)
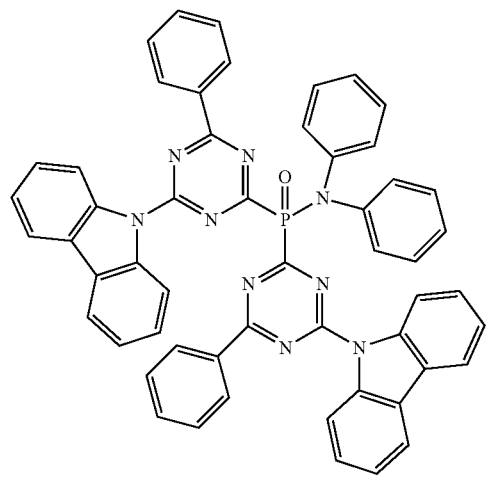
(144)
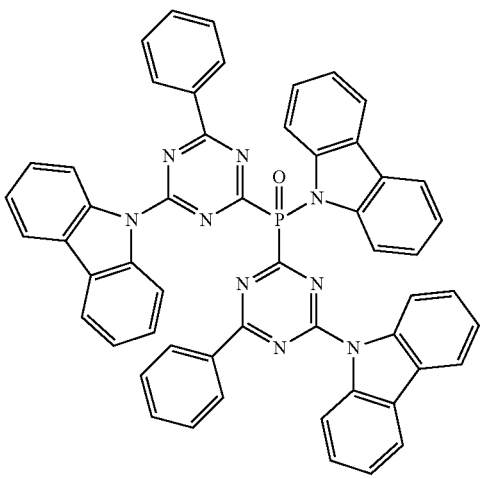
(145)
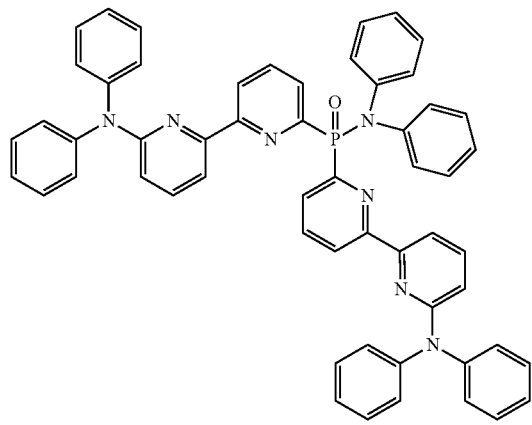
(146)
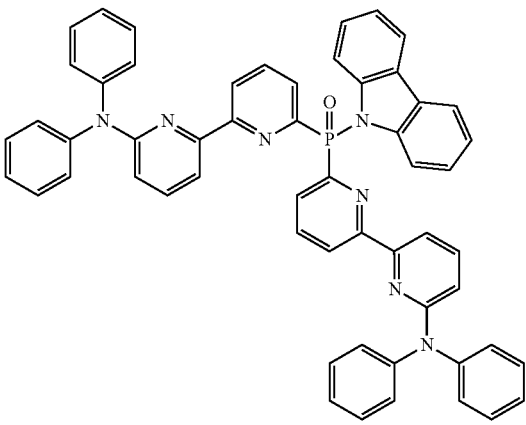

(147)
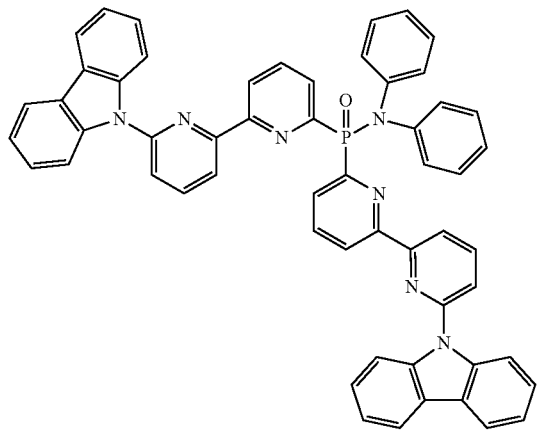

(148)
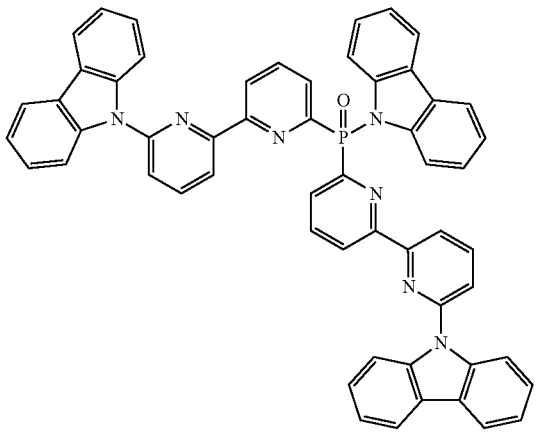

(149)
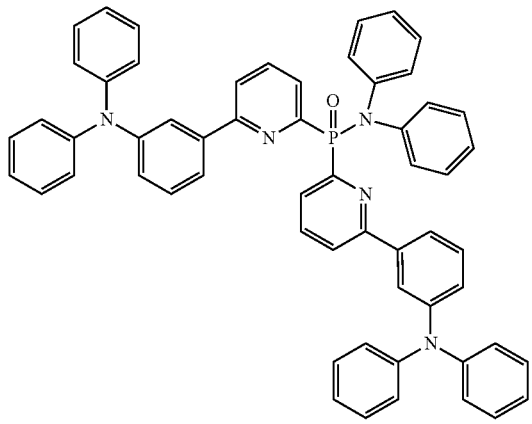

(150)
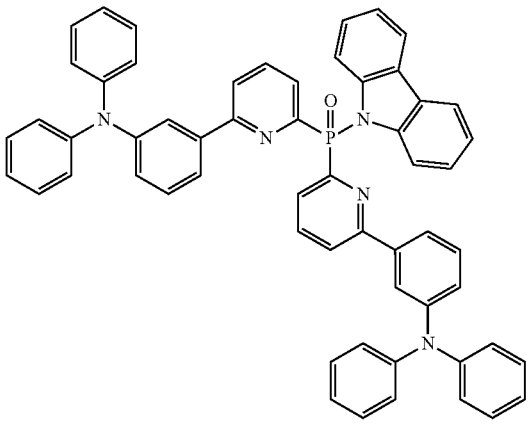

(151)
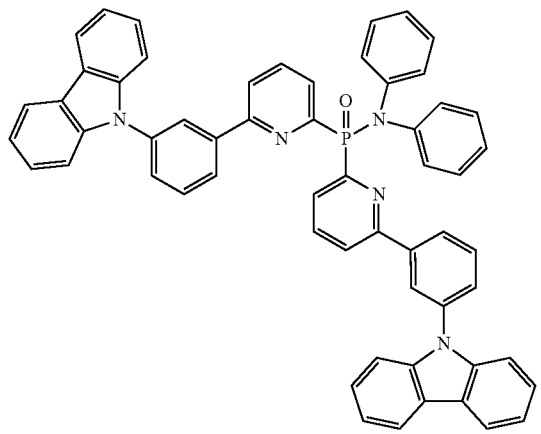

(152)
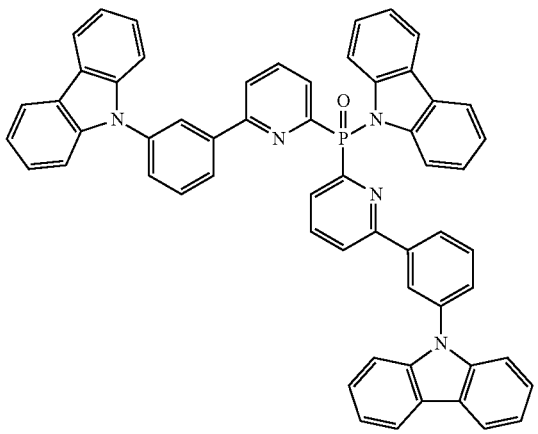

An organic EL device according to this invention has organic layers containing a light-emitting layer between an anode and a cathode piled one upon another on a substrate. The light-emitting layer here is a phosphorescent light-emitting layer. The organic EL device of this invention comprises the aforementioned phosphine oxide derivative in a light-emitting layer, an electron-transporting layer, a hole-blocking layer, or an exciton-blocking layer. The phosphine oxide derivative is preferably contained in the light-emitting layer. More preferably, the phosphine oxide derivative is contained as a host material in the light-emitting layer containing a phosphorescent dopant. In the case where the aforementioned phosphine oxide derivative is not contained in the light-emitting layer, it is contained in the electron-transporting layer, hole-blocking layer, or exciton-blocking layer. However, these layers are not essential layers and it is sufficient if the device has at least one of these layers and contains the aforementioned phosphine oxide derivative in the said one layer.

The structure of the organic EL device of this invention will be explained below with reference to the drawing, but it will not be limited to the one illustrated in the drawing.

FIG. 1 schematically shows an example of the structure of an organic EL device generally used in this invention and the symbols in FIG. 1 stand for the following: 1 for a substrate, 2 for an anode, 3 for a hole-injecting layer, 4 for a hole-transporting layer, 5 for a light-emitting layer, 6 for an electron-transporting layer, and 7 for a cathode. The organic EL device of this invention may contain an exciton-blocking layer adjoining the light-emitting layer or an electron-blocking layer between the light-emitting layer and the hole-injecting layer. The exciton-blocking layer may be disposed either on the anode side or the cathode side of the light-emitting layer or on both sides simultaneously. The organic EL device of this invention contains a substrate, an anode, a light-emitting layer, and a cathode as essential layers; in addition, the device preferably contains a hole-injecting/transporting layer and an electron-injecting/transporting layer and, further, a hole-blocking layer between the light-emitting layer and the electron-injecting/transporting layer. The term hole-injecting/transporting layer means a hole-injecting layer and/or a hole-transporting layer while the term electron-injecting/transporting layer means an electron-injecting layer and/or an electron-transporting layer.

It is possible to build a structure that is the reverse of the structure shown in FIG. 1 by piling the cathode 7, the electron-transporting layer 6, the light-emitting layer 5, the hole-transporting layer 4, and the cathode 2 one upon another in this order on the substrate 1. In this case, it is also possible to add or omit a layer or layers according to the need.

—Substrate—

The organic EL device of this invention is preferably supported by a substrate. There is no specific restriction on the substrate and any of the substrates commonly used in organic EL devices can be used. For example, a material for the substrate is selected from glass, transparent plastics, and quartz.

—Anode—

An anode made from an electrode material such as a metal of high work function (4 eV or higher), an alloy, an electrically conductive compound, and a mixture thereof is preferably used in an organic EL device. Examples of such electrode materials include electrically conductive transparent materials such as Au and other metals, CuI, indium tin oxide (ITO), $SnO_2$, and ZnO. Further, it is allowable to use an amorphous material such as IDIXO ($In_2O_3$—ZnO) that is capable of forming a transparent electrically conductive film. The anode can be formed by preparing a thin film from any of these electrode materials by a method such as vapor deposition and sputtering and then forming a pattern of desired shape on the thin film by photolithography. Or, in the case where high accuracy in patterning is not required (100 µm or more), a pattern may be formed through a mask of desired shape during vapor deposition or sputtering of the aforementioned electrode material. In the case where a material applicable by coating such as an electrically conductive organic compound is used, a wet process such as printing and coating may be used. In take out of light from the anode, the transmittance is preferably 10% or more and the sheet resistance as an anode is preferably several hundreds $\Omega/\square$ or less. Moreover, the thickness of the film is normally selected from the range of 10-1,000 nm, preferably from the range of 10-200 nm, although it varies with the material used for the film.

—Cathode—

On the other hand, a cathode made from an electrode material such as a metal of low work function (4 eV or lower) (hereinafter referred to as electron-injecting metal), an alloy, an electrically conductive compound, and a mixture thereof is used. Examples of such electrode materials include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare-earth metal. From the viewpoint of electron-injecting property and durability against degradation by oxidation, a mixture of an electron-injecting metal and a second metal which is higher in work function and more stable than the electron-injecting metal is suitable for an electrode material and examples include a magnesium/silver mixture, a magnesium/aluminum mixture, a magnesium/indium mixture, an aluminum/aluminum oxide ($Al_2O_3$) mixture, a lithium/aluminum mixture, and aluminum. The cathode is formed by forming a thin film of any of these electrode materials by a method such as vapor deposition and sputtering. The sheet resistance as a cathode is preferably several hundred $\Omega/\square$ or less and the thickness of the film is normally selected from the range of 10 nm to 5 µm, preferably from the range of 50-200 nm. Either the anode or the cathode of an organic EL device is advantageously rendered transparent or translucent to transmit the emitted light and improve the luminance.

The electrically conductive transparent material described earlier in explanation of the anode can be used in the cathode and application of this material makes it possible to fabricate a device in which both anode and cathode display a good transmittance property.

—Light-Emitting Layer—

The light-emitting layer in this invention is a phosphorescent light-emitting layer and contains a phosphorescent dopant and a host material. A material of preference for the phosphorescent dopant is an organic metal complex containing at least one metal selected from ruthenium, rhodium, palladium, silver, rhenium, osmium, iridium, platinum, and gold. Such organic metal complexes are known in the aforementioned prior-art technical documents and a suitable compound may be selected from them and used.

Preferable examples of the phosphorescent dopants include complexes containing a noble metal element such as Ir in the center, typically Ir(ppy)3, complexes such as Ir(bt)2.acac3, and complexes such as PtOEt3. Examples of these complexes are shown below, but are not limited thereto.

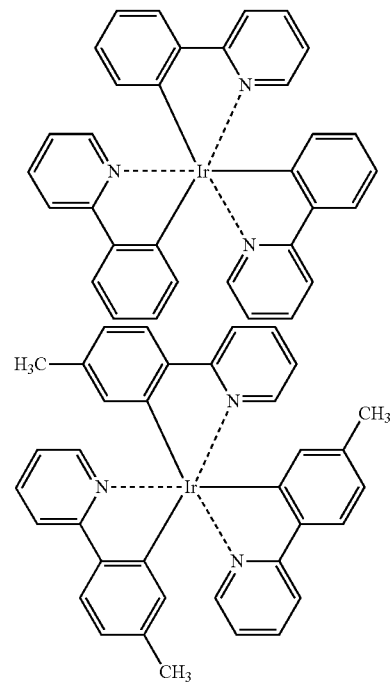

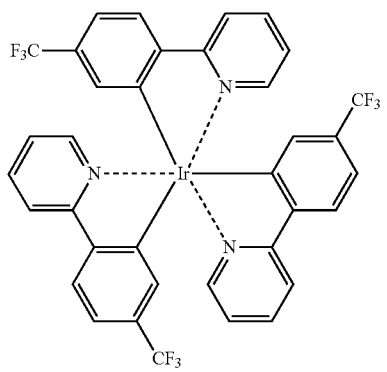
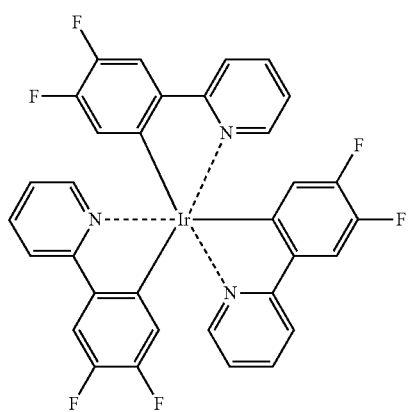
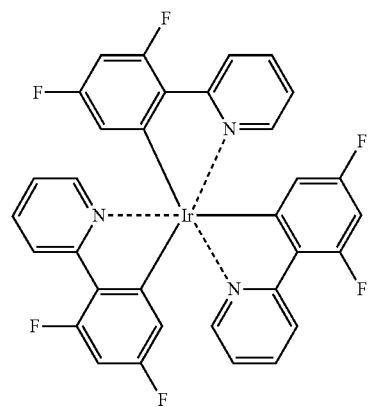
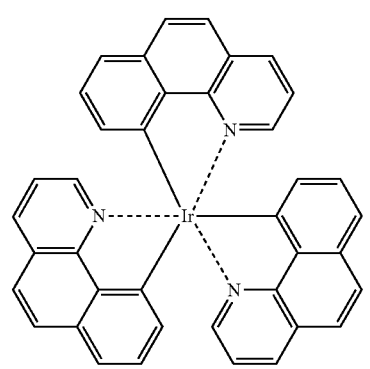
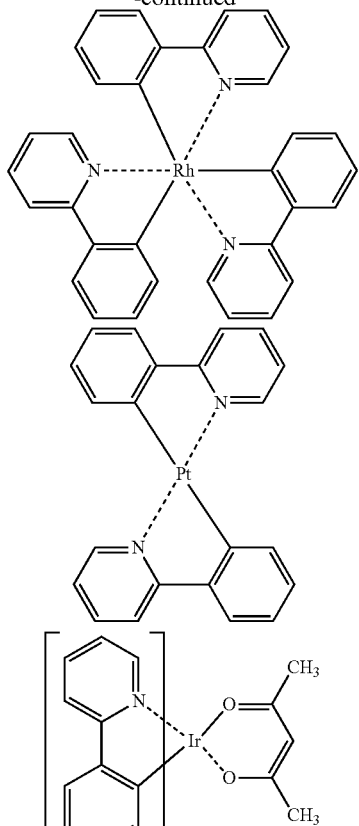
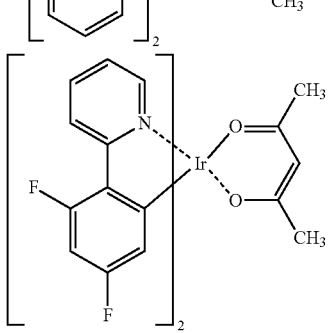
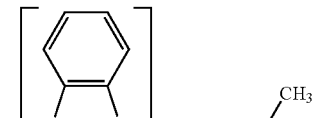
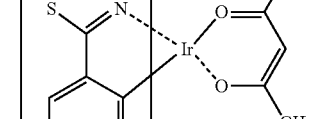
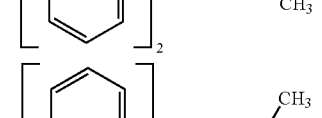
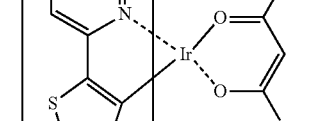

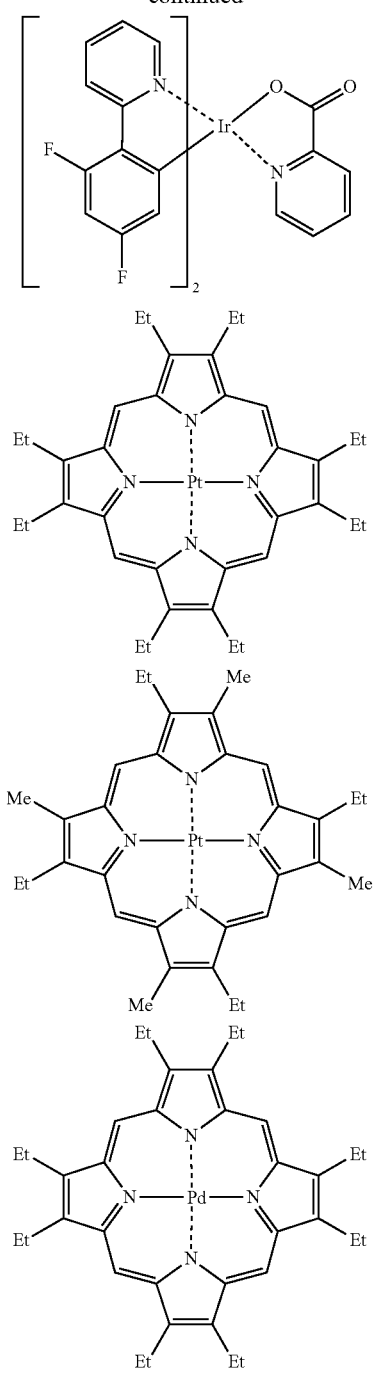

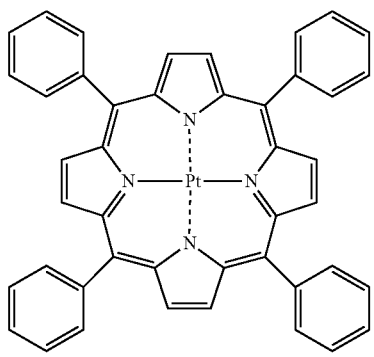

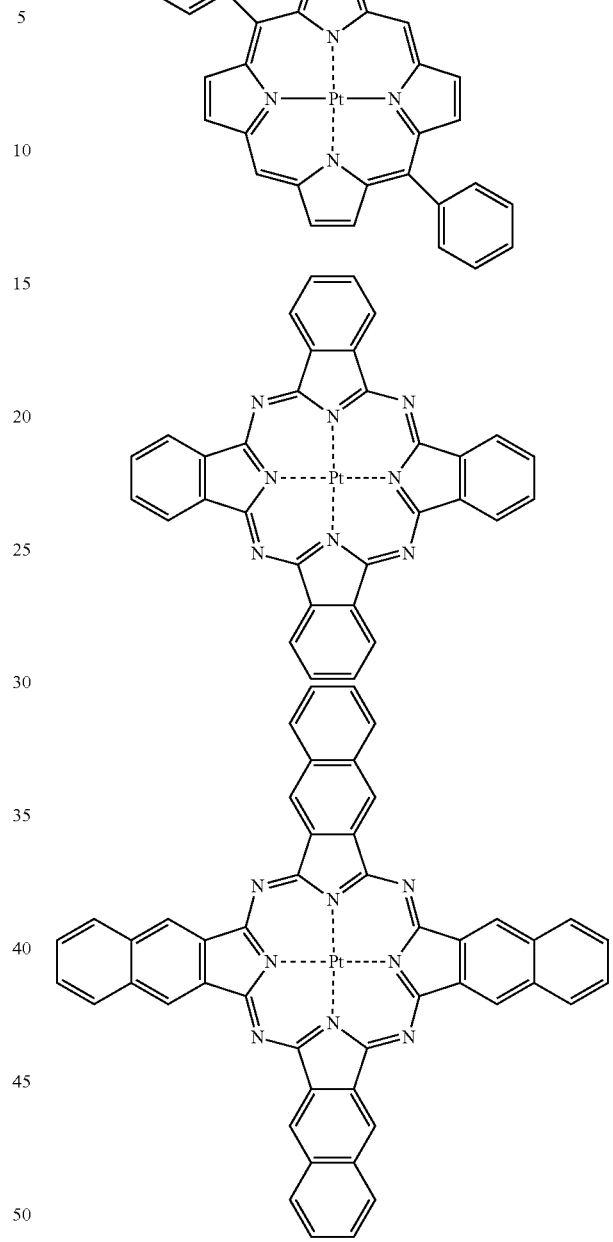

The content of the phosphorescent dopant in the light-emitting layer is preferably in the range of 5-10 wt %.

A phosphine oxide derivative represented by general formula (1) is preferably used as a host material in the light-emitting layer. However, in the case where the said phosphine oxide derivative is used in any of the organic layers other than the light-emitting layer, a host material other than a phosphine oxide derivative may be used in the light-emitting layer. Further, a phosphine oxide derivative may be used together with another host material. Still further, a phosphine oxide derivative may be used together with a plurality of known host materials.

The aforementioned another host material is preferably a compound which has a hole transport ability and an electron transport ability, prevents the wavelength of emitted light from becoming longer, and shows high glass transition temperature.

The host materials of the aforementioned kind are known in a large number of patent documents and elsewhere and a selection may be made from them. Concretely, examples of the host materials include, but not limited to, indole derivatives, carbazole derivatives, indolocarbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene-based compounds, porphyrin-based compounds, anthraquinodimethan derivatives, anthrone derivatives, diphenylquinone derivatives, thiopyran dioxide derivatives, heterocyclic tetracarboxylic acid dianhydrides such as naphthaleneperylene, phthalocyanine derivatives, a variety of metal complexes represented by metal complexes of 8-quinolinol derivatives, metal phthalocyanines, and metal complexes of benzoxazole derivatives and benzothiazole derivatives, and polymeric compounds such as polysilane-based compounds, poly(N-vinylcarbazole) derivatives, aniline-based copolymers, thiophene oligomers, polythiophene derivatives, polyphenylene derivatives, polyphenylenevinylene derivatives, and polyfluorene derivatives.

—Injecting Layer—

The injecting layer refers to a layer provided between the electrode and the organic layer in order to lower the driving voltage and improve the luminance and consists of a hole-injecting layer and an electron-injecting layer. The former is disposed between the anode and the light-emitting layer or hole-transporting layer while the latter is disposed between the cathode and the light-emitting layer or electron-transporting layer. The injecting layers may be provided according to the need.

—Hole-Blocking Layer—

The hole-blocking layer in a broad sense has a function of an electron-transporting layer. The hole-blocking layer has a role to transport electrons while preventing holes from reaching the electron-transporting layer and this layer helps to improve the probability of recombination of electrons and holes in the light-emitting layer.

A phosphine oxide derivative represented by general formula (1) is preferably used in the hole-blocking layer. In the case where a phosphine oxide derivative is used in any one of the other organic layers, a known hole-blocking material may be used in the hole-blocking layer. Further, a material useful for the electron-transporting layer to be described later may be used as a material for the hole-blocking layer according to the need.

—Electron-Blocking Layer—

The electron-blocking layer in a broad sense has a function of transporting holes. The electron-blocking layer has a role to transport holes while preventing electrons from reaching the hole-transporting layer and playing this role improves the probability of recombination of electrons and holes in the light-emitting layer. A material useful for the hole-transporting layer to be described later may be used as a material for the electron-blocking layer according to the need. The thickness of the electron-blocking layer relating to this invention is preferably 3-100 nm, more preferably 5-30 nm.

—Exciton-Blocking Layer—

The exciton-blocking layer is a layer provided to prevent excitons generated by recombination of holes and electrons in the light-emitting layer from diffusing into the charge-transporting layer and insertion of this layer can confine excitons efficiently in the light-emitting layer to enhance the luminous efficiency of the device. The exciton-blocking layer may be inserted adjoining the light-emitting layer, on the side of the anode or cathode or on both sides simultaneously.

A phosphine oxide derivative represented by general formula (1) is preferably used in the hole-blocking layer. In the case where a phosphine oxide derivative is used in any one of the other organic layers, a known hole-blocking material may be used in the hole-blocking layer.

Examples of the known exciton-blocking materials include 1,3-dicarbazolylbenzene (mCP) and bis(2-methyl-8-quinolinolato)-4-phenylphenolatoaluminum(III) (BAlq).

—Hole-Transporting Layer—

The hole-transporting layer is composed of a hole-transporting material which has a function of transporting holes and it may be constituted of a single layer or multiple layers.

The hole-transporting material has a function of injecting or transporting holes or acting as a barrier to electrons and it may be organic or inorganic. Examples of useful hole-transporting materials include triazole derivatives, oxadiazole derivatives, imidazole derivatives, polyarylalkane derivatives, pyrazoline and pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline-based copolymers, and electrically conductive oligomers, particularly thiophene oligomers. Porphyrin compounds, aromatic tertiary amine compounds, and styrylamine compounds are used preferably and aromatic tertiary amine compounds are used more preferably.

—Electron-Transporting Layer—

The electron-transporting layer is composed of an electron-transporting material which has a function of transporting electrons and it may be constituted of a single layer or multiple layers.

An electron-transporting material (which works simultaneously as a hole-blocking material in some cases) is of use as long as it has a function of transporting electrons injected from the cathode to the light-emitting layer. A phosphine oxide derivative represented by general formula (1) of this invention is preferably used in the electron-transporting layer. However, it is allowable to use a material arbitrarily selected from the known compounds, for example, from nitro-substituted fluorene derivatives, diphenylquinone derivatives, thiopyran dioxide derivatives, carbodiimides, fluorenylidenemethane derivatives, anthraquinodimethan and anthrone derivatives, and oxadiazole derivatives. Further, thiadiazole derivatives which are derived from the aforementioned oxadiazole derivatives by substituting the oxygen atom in the ring with a sulfur atom and quinoxaline derivatives whose quinoxaline ring is known as an electron-withdrawing group are useful as electron-transporting materials. Still further, polymer materials which contain the aforementioned materials in the polymer chain or as the polymer backbone are also useful.

A phosphine oxide derivative represented by general formula (1) is an excellent electron-transporting material and it is preferably contained in the light-emitting layer, the electron-transporting layer, the hole-blocking layer, or the exciton-blocking layer.

The organic EL device of this invention is applicable to a single device, a device with its structure arranged in array, or a device in which the anode and the cathode are arranged in X-Y matrix. As the organic EL device of this invention utilizes emission of light by phosphorescence, it performs at higher luminous efficiency with much more improved driving stability than the conventional devices utilizing emission of light from the excited singlet state and displays excellent performance when applied to full-color or multicolor panels.

EXAMPLES

This invention will be explained in more detail below with reference to the examples; however, this invention will not be limited to these examples and it can be reduced to practice in a variety of modes unless such practice exceeds the substance of this invention.

Synthetic Example 1

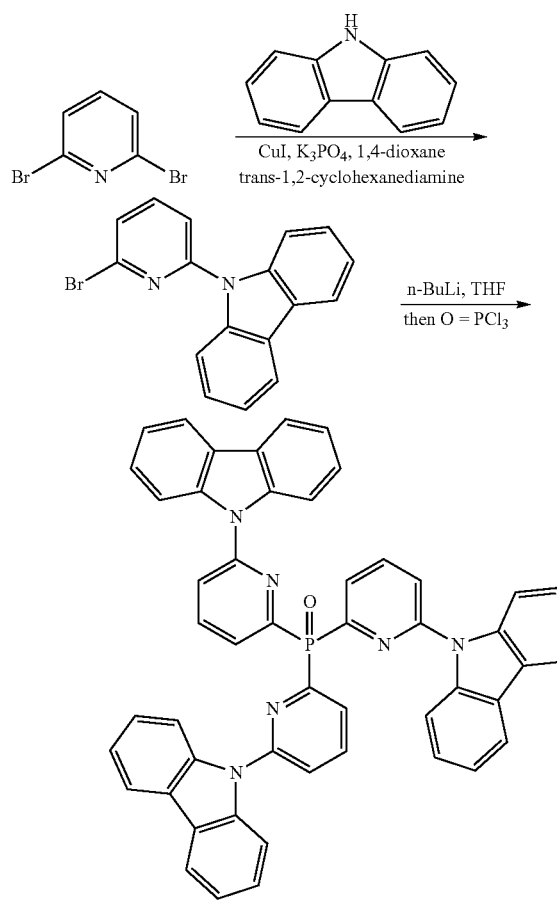

Synthesis of
tris[6-(9-carbazolyl)-2-pyridyl]phosphine oxide
(Compound 18)

Under a nitrogen atmosphere, 1.0 g (0.0088 mol) of trans-1,2-cyclohexanediamine was added to a mixture of 14.2 g (0.060 mol) of 2,6-dibromopyridine, 5.0 g (0.036 mol) of carbazole, 0.17 g (0.0019 mol) of copper(I) iodide, 31.8 g (0.15 mol) of tripotassium phosphate, and 300 ml of dehydrated 1,4-dioxane at room temperature with stirring and the mixture was heated with stirring under reflux at 100° C. for 6 hours. The reaction solution was cooled to room temperature, the inorganic salts were filtered off, and the solvent was distilled off under reduced pressure. The residue was dissolved in 200 ml of dichloromethane and washed twice with 100 ml of distilled water. The organic layer was dried over anhydrous magnesium sulfate, the magnesium sulfate was filtered off, and the solvent was distilled off under reduced pressure. The residue thus obtained was purified by reslurrying in methanol with application of heat to yield 8.2 g of 9-(6-bromo-2-pyridyl)carbazole.

Under a nitrogen atmosphere, 4.5 ml (0.0075 mol) of an n-hexane solution of n-butyllithium (1.66 mol/l) was added to a solution of 2.0 g (0.0062 mol) of 9-(6-bromo-2-pyridyl) carbazole in 10 ml of dehydrated THF at −60° C. The mixture was stirred at −60° C. for 1 hour and to this mixture was added dropwise a solution of 0.317 g (0.0021 mol) of phosphoric trichloride in 5 ml of dehydrated THF at −60° C. The reaction solution was stirred at room temperature for 3 hours and 20 ml of a saturated aqueous ammonium chloride solution was added. This solution was concentrated and then extracted twice with 50 ml of dichloromethane. The organic layer was dried over anhydrous magnesium sulfate, the magnesium sulfate was filtered off, and the solvent was distilled off under reduced pressure. The residue thus obtained was purified by silica gel column chromatography (eluent: hexane/ethyl acetate=1/1), then further purified by reslurrying in methanol with application of heat to yield 0.93 g of Compound 18: melting point, 299° C.; APCI-TOFMS, m/z 777 [M+H]+.

Synthetic Example 2

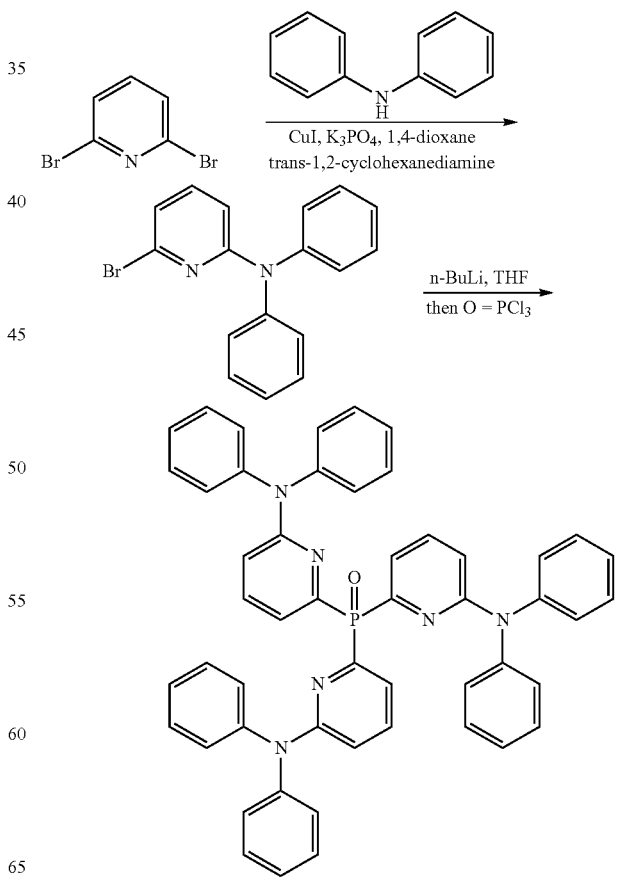

Synthesis of
tris[6-(N,N-diphenylamino)-2-pyridyl]phosphine
oxide (Compound 10)

Compound 10 was synthesized from 2,6-dibromopyridine and diphenylamine as in Synthetic Example 1.

Synthetic Example 3

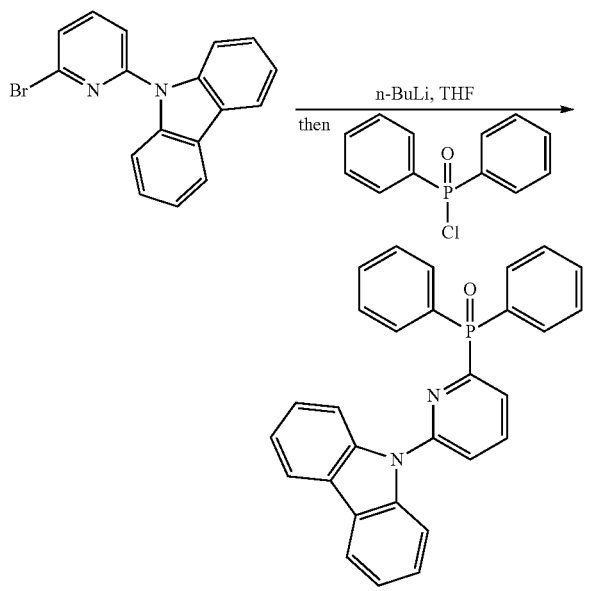

Synthesis of
[6-(9-carbazolyl)-2-pyridyl]diphenylphosphine oxide
(Compound 58)

Compound 58 was synthesized from 9-(6-bromo-2-pyridyl)carbazole and diphenylphosphinic chloride as in Synthetic Example 1.

Comparative Example 1

The constituent layers in thin film were formed one upon another on a glass substrate on which a 110 nm-thick indium tin oxide (ITO) anode had been formed while applying the vacuum vapor deposition process at a degree of vacuum of $4.0 \times 10^{-4}$ Pa. First, a hole-injecting layer was formed by depositing copper phthalocyanine (CuPC) on the ITO anode to a thickness of 30 nm. Then, a hole-transporting layer was formed by depositing 4,4'-bis[N-(1-naphthyl)-N-phenylamino]biphenyl (NPD) to a thickness of 80 nm. A light-emitting layer was then formed on the hole-transporting layer by co-depositing 1,3-di(9-carbazolyl)benzene (mCP) as a host material and bis[2-(4,6-difluorophenyl)pyridinato-N,C2']iridium(III) picolinate (FIrpic), a phosphorescent blue light-emitting material, from different evaporation sources to a thickness of 35 nm. The concentration of FIrpic was 8.0%. An electron-transporting layer was then formed by depositing tris(8-hydroxyquinolinato)aluminum(III) (Alq3) to a thickness of 25 nm. Further, an electron-injecting layer was formed on the electron-transporting layer by depositing lithium fluoride (LiF) to a thickness of 0.5 nm. Finally, an electrode was formed on the electron-injecting layer by depositing aluminum (Al) to a thickness of 170 nm to complete the fabrication of an organic EL device that is constructed as illustrated in FIG. 1 with addition of the electron-injecting layer between the cathode and the electron-transporting layer.

The organic EL device thus obtained was connected to an outside power source and, when direct current voltage was applied, the device was confirmed to display the luminous characteristics shown in Table 1. In Table 1, the luminance, voltage, and luminous efficiency were measured at 2.5 mA/cm$^2$ and the luminance half-life at 5.0 mA/cm$^2$. The maximum wavelength of the emission from the device is 470 nm and this proves that the emitter is FIrpic.

Example 1

An organic EL device was fabricated as in Comparative Example 1 except that Compound 18 was used as a host material in the light-emitting layer. The maximum wavelength of the emission from the device is 470 nm and the emitter is identified as FIrpic. The luminous characteristics are shown in Table 1.

Example 2

An organic EL device was fabricated as in Comparative Example 1 except that Compound 10 was used as a host material in the light-emitting layer. The maximum wavelength of the emission from the device is 470 nm and the emitter is identified as FIrpic. The luminous characteristics are shown in Table 1.

Example 3

An organic EL device was fabricated as in Comparative Example 1 except that Compound 58 was used as a host material in the light-emitting layer. The maximum wavelength of the emission from the device is 470 nm and this proves that light is emitted from FIrpic. The luminous characteristics are shown in Table 1.

Comparative Example 2

An organic EL device was fabricated as in Comparative Example 1 except that Compound 8 was used as a host material in the light-emitting layer. The maximum wavelength of the emission from the device is 470 nm and the emitter is identified as FIrpic. The luminous characteristics are shown in Table 1.

Comparative Example 3

An organic EL device was fabricated as in Comparative Example 1 except that Compound 9 was used as a host material in the light-emitting layer. The maximum wavelength of the emission from the device is 470 nm and the emitter is identified as FIrpic. The luminous characteristics are shown in Table 1.

TABLE 1

| | Host material for light-emitting layer | Luminance (cd/m$^2$) | Voltage (V) | Luminous efficiency (lm/W) | Luminance half-life (hrs) |
| --- | --- | --- | --- | --- | --- |
| Ex. 1 | Compound 18 | 1314 | 9.5 | 4.3 | 132 |
| Ex. 2 | Compound 10 | 1231 | 9.5 | 4.1 | 120 |
| Ex. 3 | Compound 58 | 1180 | 9.4 | 3.9 | 146 |

TABLE 1-continued

|  | Host material for light-emitting layer | Luminance (cd/m²) | Voltage (V) | Luminous efficiency (lm/W) | Luminance half-life (hrs) |
|---|---|---|---|---|---|
| Comp. Ex. 1 | mCP | 875 | 13.2 | 2.1 | 53 |
| Comp. Ex. 2 | Compound 8 | 984 | 9.8 | 3.2 | 84 |
| Comp. Ex. 3 | Compound 9 | 958 | 10.2 | 3.0 | 69 |

Example 4

An organic EL device was fabricated as in Comparative Example 1 except that Compound 18 was used as a material for the electron-transporting layer. The maximum wavelength of the emission from the device is 470 nm and the emitter is identified as Flrpic. The luminous characteristics are shown in Table 2.

TABLE 2

|  | Material for electron-transporting layer | Luminance (cd/m²) | Voltage (V) | Luminous efficiency (lm/W) | Luminance half-life (hrs) |
|---|---|---|---|---|---|
| Ex. 4 | Compound 18 | 1063 | 9.1 | 3.7 | 88 |
| Comp. Ex. 1 | Alq3 | 875 | 13.2 | 2.1 | 53 |

Example 5

An organic EL device was fabricated as in Comparative Example 1 except that Compound 18 was deposited to a thickness of 10 nm as a material for the exciton-blocking layer after formation of the light-emitting layer and Alq3 was deposited to a thickness of 15 nm as a material for the electron-transporting layer. The organic EL device thus obtained has the layered structure illustrated in FIG. 1 to which the exciton-blocking layer is added between the light-emitting layer and the electron-transporting layer. The maximum wavelength of the emission from the device is 470 nm and the emitter is identified as Flrpic. The luminous characteristics are shown in Table 3.

TABLE 3

|  | Material for exciton-blocking layer | Luminance (cd/m²) | Voltage (V) | Luminous efficiency (lm/W) | Luminance half-life (hrs) |
|---|---|---|---|---|---|
| Ex. 5 | Compound 18 | 1109 | 9.8 | 3.6 | 79 |
| Comp. Ex. 1 | none | 875 | 13.2 | 2.1 | 53 |

INDUSTRIAL APPLICABILITY

Suppose attention is paid to the frontier orbital of a phosphine oxide derivative to be used in the organic EL device of this invention. The lowest unoccupied molecular orbital (LUMO) extends widely over a portion of the phosphine oxide group where direct linkage of the nitrogen heterocycle occurs or over a moiety shown by $L_1$-P=O. This facilitates giving and receiving of electrons between molecules and affords a good electron transport property. On the other hand, the highest occupied molecular orbital (HOMO) exists over $NAr_1Ar_1$ located on the outer side of the molecule and this facilitates giving and receiving of holes between molecules. As a result, the said phosphine oxide derivative displays a good balance of the injection/transport properties of electrical charges.

A compound having both diarylamine and phosphine oxide moieties improves its electron injection/transport property by possession of a nitrogen heterocycle linked directly to phosphine oxide and, at the same time, maintains a good hole injection/transport property. In consequence, the use of the said compound as a phosphorescent host material in an organic EL device reduces the driving voltage of the device, improves the balance of charges in the light-emitting layer, and widens the region of recombination of holes and electrons to enhance the luminous efficiency. Further, since the lowest triplet excitation energy of this phosphorescent host material is sufficiently high to confine the lowest triplet excitation energy of a dopant, the transfer of the triplet excitation energy from the dopant to the host molecule is effectively inhibited. The aforementioned properties enable the organic EL device of this invention to achieve low driving voltage and high luminous efficiency.

In the case where the said compound is used as a material for the electron-transporting layer or hole-blocking layer, it reduces the driving voltage and enhances the luminous efficiency of the device by virtue of its good electron injection/transport property.

Further, since the lowest triplet excitation energy of a phosphine oxide derivative is sufficiently high to confine the lowest triplet excitation energy of a dopant, a phospine oxide derivative used as a material for the exciton-blocking layer can effectively inhibit the transfer of the triplet excitation energy from the dopant to the adjacent layer containing the said phosphine oxide derivative and the luminous efficiency can be enhanced.

In addition, phosphine oxide derivatives show good properties in the amorphous form, high heat stability, and electrochemical stability. The aforementioned properties have helped to realize organic EL devices of long driving life and good durability.

The organic EL device of this invention satisfies a level of performance required for practical use with respect to the luminous characteristics, driving life, and durability and is of high technical value because of its potential applicability to flat panel displays (for example, mobile phone display devices, vehicle-mounted display devices, office computer display devices, and television sets), light sources utilizing the characteristics of planar light emitters (for example, illumination, light sources for copiers, and backlight sources for liquid crystal displays and instruments), signboards, and beacon lights.

The invention claimed is:

1. An organic electroluminescent device constituted of an anode, organic layers comprising a phosphorescent light-emitting layer, and a cathode piled one upon another on a substrate wherein at least one layer selected from the group consisting of a phosphorescent light-emitting layer, an electron-transporting layer, a hole-blocking layer, and an exciton-blocking layer comprises a phosphine oxide derivative represented by general formula (1):

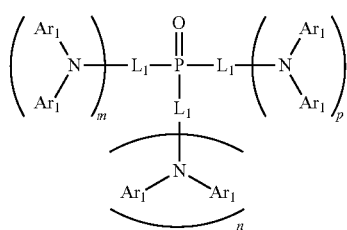

(1)

wherein $L_1$ is independently a direct bond or an aromatic group with a valence of 1-3 formed by removing 1-3 hydrogen atoms from an aromatic compound represented by the following formula (1a), (1b), or (1c) and at least one of $L_1$s is not a direct bond; $Ar_1$ is independently an aromatic hydrocarbon group of 6-20 carbon atoms or an aromatic heterocyclic group of 3-20 carbon atoms and the two $Ar_1$ groups linked to the same nitrogen atom may join together directly or through another atom to form a nitrogen heterocycle and may further form a fused ring together with the said nitrogen heterocycle; the aforementioned aromatic hydrocarbon group or aromatic heterocyclic group may have substituents; m, n, and p each is independently an integer of 0-2 and m+n+p is 1-6;

in formula (1a), (1b), or (1c), X is independently a substituted or unsubstituted methine group or nitrogen and, when $L_1$ is a divalent or trivalent aromatic group, at least one of Xs is nitrogen; when X is a substituted methine group, the substituent therein is independently an alkyl group of 1-6 carbon atoms, an alkoxyl group of 1-6 carbon atoms, an aryloxyl group of 3-20 carbon atoms, an aromatic hydrocarbon group of 6-20 carbon atoms, or an aromatic heterocyclic group of 3-20 carbon atoms:

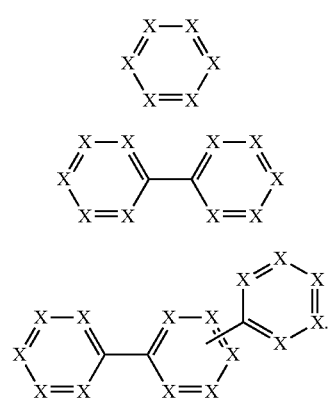

2. An organic electroluminescent device as described in claim 1 wherein the phosphine oxide derivative represented by general formula (1) is represented by general formula (2):

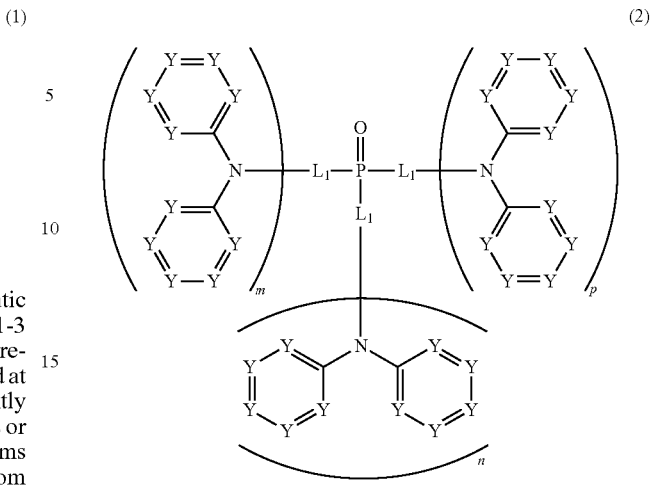

wherein Y is independently a substituted or unsubstituted methine group or nitrogen; when Y is a substituted methine group, the substituent therein is independently an alkyl group of 1-6 carbon atoms, an alkoxyl group of 1-6 carbon atoms, an aryloxyl group of 3-20 carbon atoms, an aromatic hydrocarbon group of 6-20 carbon atoms, an aromatic heterocyclic group of 3-20 carbon atoms, or an amino group substituted with an aromatic hydrocarbon group of 6-14 carbon atoms or with an aromatic heterocyclic group of 3-14 carbon atoms; the aromatic hydrocarbon groups or aromatic heterocyclic groups linked to the nitrogen atom of the said amino group may join together directly or through another atom to form a nitrogen heterocycle containing the said nitrogen atom and may further form a fused ring together with the said nitrogen heterocycle; the two six-membered aromatic hydrocarbon groups or six-membered aromatic heterocyclic groups existing as substituents on the nitrogen atom that is linked to $L_1$ may join together directly or through another atom to form a nitrogen heterocycle containing the said nitrogen that is linked to $L_1$ and may further form a fused ring together with the said nitrogen heterocycle; $L_1$, m, n, and p respectively have the same meaning as in general formula (1).

3. An organic electroluminescent device as described in claim 1 wherein the layer comprising the phosphine oxide derivative is the light-emitting layer containing a phosphorescent dopant.

4. An organic electroluminescent device as described in claim 2 wherein the layer comprising the phosphine oxide derivative is the light-emitting layer containing a phosphorescent dopant.

* * * * *